(12) United States Patent
Finkelstein et al.

(10) Patent No.: US 6,248,937 B1
(45) Date of Patent: Jun. 19, 2001

(54) TRANSCRIPTION FACTOR AND METHOD FOR REGULATION OF SEED DEVELOPMENT, QUALITY AND STRESS-TOLERANCE

(75) Inventors: Ruth R. Finkelstein; Tim Lynch, both of Santa Barbara, CA (US); Howard M. Goodman, Newton Centre; Ming-Li Wang, Cambridge, both of MA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/300,672

(22) Filed: Apr. 27, 1999

Related U.S. Application Data

(60) Provisional application No. 60/083,334, filed on Apr. 27, 1998.

(51) Int. Cl.[7] ............................ C12N 15/29; C12N 15/82; C12N 15/84; C12N 15/90; A01H 5/00
(52) U.S. Cl. .................... 800/290; 435/69.1; 435/320.1; 435/469; 435/470; 536/23.6; 800/287; 800/294; 800/298; 800/312; 800/314; 800/320; 800/320.3
(58) Field of Search .................. 435/69.1, 320.1, 435/410, 419, 431, 468, 469, 470; 536/23.6; 800/278, 287, 294, 295, 298, 292, 293, 290, 312, 314, 320, 320.3

(56) References Cited

PUBLICATIONS

Finkelstein et al, Plant Cell, vol. 10, lines 1043–1054, 1998.*

* cited by examiner

*Primary Examiner*—Gary Benzion
*Assistant Examiner*—Ashwin D. Mehta
(74) *Attorney, Agent, or Firm*—Hana Verny

(57) ABSTRACT

Identification, cloning and sequencing of the Arabidopsis ABI4 gene involved in seed response to abscisic acid (ABA) that regulates production of seed nutrient reserves and desiccation protectants. A method for regulating seed development, viability, stress-tolerance and nutrient reserves.

13 Claims, 10 Drawing Sheets

FIG. 4A-1

```
  1 AATCGACCATTCACAACGATGACATTCAAACACTCTTCAGTTTCCCTTCCTTCTTGATTC
 61 GTCCTCTCCACTATTTTTCTCAATTTCTTTAATCTCTCTCTTTCTCTCTCTACTTCCTCT
121 TCCTCTTCTTCTTCTTCTTCTTCTTCATCTATGGACCCTTTAGCTTCCCAACATCAACAC
                                    M  D  P  L  A  S  Q  H  Q  H

181 AACCATCTGGAAGATAATAACCAAACCCTAACCCATAATAATCCTCAATCCGATTCCACC
 11  N  H  L  E  D  N  N  Q  T  L  T  H  N  N  P  Q  S  D  S  T

241 ACCGACTCATCAACTTCCTCCGCTCAACGCAAACGCAAAGGCAAGGTGGTCCGGACAAC
 31  T  D  S  S  T  S  S  A  Q  R  K  R  K  G  K  G  G  P  D  N

301 TCCAAGTTCCGTTACCGTGGCGTTCGACAAAGAAGCTGGGGCAAATGGGTCGCCGAGATC
 51  S  K  F  R  Y  R  G  V  R  Q  R  S  W  G  K  W  V  A  E  I

361 CGAGAGCCACGTAAGCGCACTCGCAAGTGGCTTGGTACTTTCGCAACCGCCGAAGACGCC
 71  R  E  P  R  K  R  T  R  K  W  L  G  T  F  A  T  A  E  D  A

421 GCACGTGCCTACGACCGGGCTGCCGTTTACCTATACGGGTCACGTGCTCAGCTCAACTTA
 91  A  R  A  Y  D  R  A  A  V  Y  L  Y  G  S  R  A  Q  L  N  L

481 ACCCCTTCGTCTCCTTCCTCCGTCTCTTCCTCTTCCTCCTCCGTCTCCGCCGCTTCTTCT
111  T  P  S  S  P  S  S  V  S  S  S  S  S  S  V  S  A  A  S  S

541 CCTTCCACCTCCTCTTCCTCCACTCAAACCCTAAGACCTCTCCTCCCTCGCCCCGCCGCC
131  P  S  T  S  S  S  S  T  Q  T  L  R  P  L  L  P  R  P  A  A
                                    Δ
601 GCCACCGTAGGAGGAGGAGCCAACTTTGGTCCGTACGGTATCCCTTTTAACAACAACATC
151  A  T  V  G  G  G  A  N  F  G  P  Y  G  I  P  F  N  N  N  I

661 TTCCTTAATGGTGGGACCTCTATGTTATGCCCTAGTTATGGTTTTTTCCCTCAACAACAA
171  F  L  N  G  G  T  S  M  L  C  P  S  Y  G  F  F  P  Q  Q  Q

721 CAACAACAAAATCAGATGGTCCAGATGGGACAATTCCAACACCAACAGTATCAGAATCTT
191  Q  Q  Q  N  Q  M  V  Q  M  G  Q  F  Q  H  Q  Q  Y  Q  N  L

781 CATTCTAATACTAACAATAACAAGATTTCTGACATCGAGCTCACTGATGTTCCGGTAACT
211  H  S  N  T  N  N  N  K  I  S  D  I  E  L  T  D  V  P  V  T

841 AATTCGACTTCGTTTCATCATGAGGTGGCGTTAGGGCAGGAACAAGGAGGAAGTGGGTGT
231  N  S  T  S  F  H  H  E  V  A  L  G  Q  E  Q  G  G  S  G  C

901 AATAATAATAGTTCGATGGAGGATTTGAACTCTCTAGCTGGTTCGGTGGGTTCGAGTCTA
251  N  N  N  S  S  M  E  D  L  N  S  L  A  G  S  V  G  S  S  L

961 TCAATAACTCATCCACCGCCGTTGGTTGATCCGGTATGTTCTATGGGTCTGGATCCGGGT
271  S  I  T  H  P  P  P  L  V  D  P  V  C  S  M  G  L  D  P  G
```

FIG. 4A-2

```
1021  TATATGGTTGGAGATGGATCTTCGACCATTTGGCCTTTTGGAGGAGAAGAAGAATATAGT
 291   Y  M  V  G  D  G  S  S  T  I  W  P  F  G  G  E  E  E  Y  S

1081  CATAATTGGGGGAGTATTTGGGATTTTATTGATCCCATCTTGGGGGAATTCTATTAATTT
 311   H  N  W  G  S  I  W  D  F  I  D  P  I  L  G  E  F  Y  *

1141  GTTTTTGTGGAAGATCATATTATATACGATGAGCATCCCTAAGGTCGGTCAAGAGCATTG
1201  GAGATTCATTGTTGAGAGGAATCAAAGAGATTGCATTCTATGAGGAGCTCTGCATGCAAA
1261  ATTTTGGAGGATTTTTTTACTACCTATAGAGATAAATAAGAGGGTATTTTTATTATTTTT
1321  TTGAAGATTTTTATTTTCAAGGAATTCGTAAAAGAGATTACGGTTCCAATAAAGTATGTA
1381  TATGTGGAAGAGAATCGGAGGAGATGGTGGAAAGTTGTATGGGAATTTTATTGGTTCAAC
1441  ACTTCCTTCACAGTGTGCCTACCTTAATATATAATTATTGATAGGATATGATAATTTCTG
```

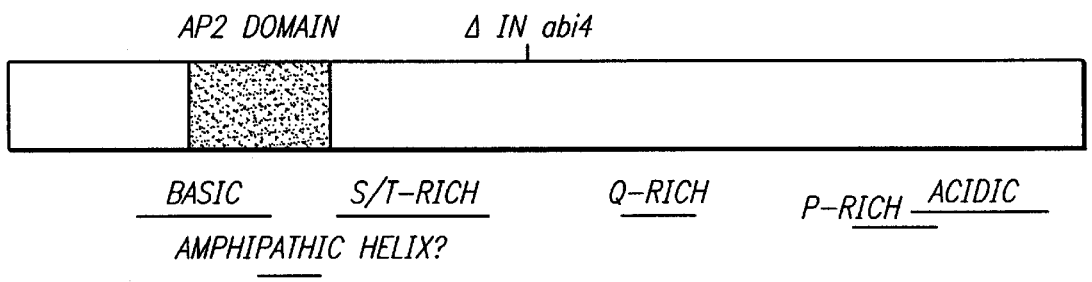

```
          YRGVR.QRSWG KWVAEIREPR KRT.RKWLGT FATAEDAARA YDRAAVYLYG SRAQLNLTPS
ABI4      ******.**NS*  ****S*V****N *K*.*I***** *Q****H***** H*V**LA*R* RS*C**FADS
CBF1      ****.H  SS****HSI LK*.*I*Q** *ES****** E**RLMC* T**RT*FPYN
Lpp1zo2   ****.P  A*****D*N *AA.*V***** *D**EL* KFEFR* HK*K**FPEH
AtCdinp   ******.K*N**  ****S******* *KS.*I***** *PSP*M***** H*V**LSIK* AS*I**FPDL
Tiny      ******.R*P**  *FA*****D*A *NGA*V***** YE*D*E***I* KYRMR* *K*H**FPHR
EREBP1    ****I*.K*P  A***D *GV.*V***** *N**E*M* VKQIR* DK*K**FPDL
AtEBP     **TFYRRTG  RWESHIWDCG K..QVYG* DHA** **IKFR*V E*DI*FNIDD
Ap2r1     ****TLHKC*R  *E*RMGQFLG KKYVYLGLF. D*EVE****** *K**IKCN*K D*VT*FDPSI
Ap2r2

EREBP-like         i               fv  ke                      s  y          i                v
Consensus  yRGvr..R.wG  +waAEIrd..  ....R.WLGt  f.t.eeAA+A  YD.Aa...+G  ..A..NFp..
```

TRANSCRIPTION FACTOR AND METHOD FOR REGULATION OF SEED DEVELOPMENT, QUALITY AND STRESS-TOLERANCE

This invention is based on and claims priority of the Provisional Application Serial No. 60/083,334 filed on Apr. 27, 1998.

This invention was made with Government support under Grant No. DCB9105241, awarded by the National Science Foundation and Grant No. 95-37304-2217, awarded by the US Department of Agriculture. The Government has certain rights to this invention.

BACKGROUND OF THE INVENTION

1. Field of the Invention

This invention concerns identification, cloning and sequencing of an Arabidopsis gene encoding a transcription factor involved in response to abscisic acid (ABA) that regulates production of seed nutrient reserves and desiccation protectants. In particular, the invention concerns identification, cloning and sequencing of the Arabidopsis ABI4 locus. ABI4 is involved in regulating seed development, production of seed nutrient reserves and desiccation protectants, and also in some ABA responses of seedlings. Over expression of the ABI4 locus is involved in modification of seed quality and vegetative responses to ABA, including tolerance to stresses such as drought or salinity. The invention also concerns a method for regulation of seed viability, production of nutrient reserves and desiccation protectants in seeds, and vegetative stress tolerance.

2. Background and Related Disclosures

Seeds, fertilized ovules containing embryos which upon germination form new plants, are important as a means of carrying plant life over periods unfavorable for growth and also as a means of distributing the plant in time and in space. The yield, quality and viability of a seed lot or crop depend on its genetic background, nutrient content and ability to germinate readily and produce a normal plant even after long term storage at variable temperatures. In addition, the general health of the plants during vegetative growth will affect their ability to support the energy demands of seed set.

It would be, therefore, advantageous to have a means to regulate a seed's viability by increasing its storage-life and increasing the plant's tolerance of stresses that may be encountered during vegetative growth.

Abscisic acid (ABA) regulates many agronomically important aspects of plant development, including synthesis of seed storage proteins and lipids (*Plant Sci.*, 61:213–217 (1988) and *Plant Hormones: Physiology, Biochemistry and Molecular Biology*, 2nd ed., P. J. Davies, Ed., Norwell, Mass., Kluwer Academic Publisher, 671–697 (1995)), seed desiccation tolerance and dormancy (*Arabidopsis*, C. Somerville and Meyerowitz, E. M., Eds., Cold Spring Harbor: Cold Spring Harbor Laboratory Press, pp. 313–334 (1994)), as well as stomatal closure (*Encyclopedia of Plant Physiology*, W. Haupt and M. Feinlieb, Eds., VII. Springer-Verlag, 383–441 (1979)). In addition, ABA can induce tolerance of water-, salt- and cold stress (*Ann. Rev. Plant Physiology*, 39: 439–473 (1988); *Plant Molecular Biology*, 26: 1557–1577, (1994)).

Genetic studies, especially in Arabidopsis, have identified a large number of loci involved in ABA response (*Ann. Rev. Plant Physiol. Plant Mol. Biol.*, 49:199–222 (1998)). The ABA response mutant phenotypes include defects in storage reserve accumulation, maturation, and dormancy of seeds, and altered ABA or stress-sensitivity for control of germination inhibition, stomatal regulation, root growth, and expression of a variety of stress-induced genes. These "ABA-insensitive" (ABI) phenotypes are extensively reviewed in Arabidopsis, C. Somerville and E. Meyerowitz, Eds., (Cold Spring Harbor: Cold Spring Harbor Press, pp. 523–553 (1994)).

Most of the ABA response mutants have relatively stage-specific defects, primarily affecting either vegetative or reproductive growth. Digenic analyses indicate that these loci are likely to be acting in multiple overlapping response pathways (*Plant Physiology*, 94: 1172–1179, (1990), *Ann. Rev. Plant Physiol. Plant Mol. Biol.*, 49:199–222 (1998)). The abi1 and abi2 mutants primarily affect vegetative growth, resulting in reduced tolerance of stresses such as drought. The abi3 mutants have defects in seed development, but wild-type vegetative growth. The abi3 null mutant seeds fail to become desiccation tolerant and therefore cannot endure any period of dry storage, demonstrating the extreme importance to seed viability of the ABI3-dependent signaling pathway.

To date, only 5 mutationally identified ABA response loci have been cloned. These represent only three classes of protein: two orthologous transcriptional regulators (Viviparous 1 (Vp1)) of maize as described in *Plant Cell*, 1: 523–532(1989) and ABA-insensitive 3 (ABI3) of Arabidopsis (*Plant Cell*, 4: 1251–1261 (1992)), two highly homologous members of the protein phosphatase 2C family, namely ABI1 and ABI2 of Arabidopsis (*Science*, 264: 1452–1455 (1994), *Plant Cell*, 9: 759–771 (1997)), and a farnesyl transferase encoded by Enhanced Response to ABA 1 (ERA1) of Arabidopsis (*Science*, 273: 1239–1241 (1996)).

The roles of ABI1, ABI2 and ABI3 relative to each other are complex. Although ABI3 is normally seed-specific and consequently is not involved in stomatal regulation, ectopic expression of ABI3 in vegetative tissue suppresses the wilty phenotype of the abi1 mutation.

Ectopic vegetative expression of ABI3 also results in ABA-inducible vegetative expression of a subset of the genes regulated by ABI3 in seeds, e.g. those encoding storage proteins (*Plant Cell*, 6:1567–1582 (1994)). However, there are some limitations to the efficacy of ABI3 in extending this "seed-specific" developmental program into vegetative growth: not all ABI3-regulated genes become ABA-inducible and this ABA/ABI3-dependent expression may require yet another element of the signal transduction pathway involving ABI3.

Although the genetic regulation of ABA response described previously is complex and still only poorly understood, it is clear that these ABA response loci play an important role in regulating seed quality and survival abilities.

It has now been discovered that yet another gene, the Arabidopsis ABI4 locus, is involved in important aspects of seed nutritional quality and survival properties, can regulate ABA responsiveness of vegetative tissue, and acts as an element of the signal transduction pathway of ABI3. The role of ABI4 in regulating seed quality is reflected in the fact that abi3,abi4 digenic mutants have reduced longevity where seeds remain viable for only months, rather than years, compared to their monogenic parents.

It is, therefore, a primary objective of this invention to provide and identify a new transcription factor regulating seed development, seed viability, seed quality and vegetative stress tolerance and to provide a method for modification of seed properties by manipulating seed genetic material.

SUMMARY

One aspect of the current invention is identification of a gene, the Arabidopsis ABI4 locus, encoding a novel transcription factor that regulates seed development, viability, quality, survival properties, and some ABA responses of seedlings.

Another aspect of the current invention is identification, cloning and sequencing of an Arabidopsis gene identified as the ABI4 gene.

Still another aspect of the current invention is a DNA sequence identified as SEQ ID NO:1 (gene bank accession # AF040959) or a mutant or a variant thereof.

Still yet another aspect of the current invention is a predicted amino acid sequence identified as SEQ ID NO:2 or a mutant or a variant thereof.

Still yet another aspect of the current invention is a method for alteration of seed properties by regulating expression of the protein encoded by the ABI4 gene.

Yet another aspect of the current invention is a method for production of transgenic plants having altered survival properties, said method comprising expressing a protein having a sequence SEQ ID NO:2 or a mutant or variant thereof.

Still another aspect of the current invention is a mutant abi4 (SEQ ID NO: 3) of the ABI4 gene comprising a single base pair deletion.

Yet another aspect of the current invention is a method for enhancing effectiveness of ectopic ABI3 expression via ABA-inducible gene expression to increase stress resistance and/or effect synthesis of storage proteins, desiccation protectants or seed oil in vegetative tissues.

Still yet another aspect of the current invention is use of the ABI4 gene as a source of promoter for low level ectopic expression of a regulatory gene in seeds.

BRIEF DESCRIPTION OF DRAWINGS

FIG. 4A shows a nucleotide sequence (SEQ ID NO: 1) and a predicted amino acid sequence (SEQ ID NO: 2). FIG. 4B shows the domain structure of the ABI4 protein.

FIG. 5 shows regions of homology conserved between ABI4 and other AP2-domain proteins.

FIG. 7(A–B) illustrates developmental specificity of ABI4 mRNA accumulation.

FIG. 11(A–B) shows the effects of ABI4 ectopic expression on root growth.

DEFINITIONS

Figure 1:
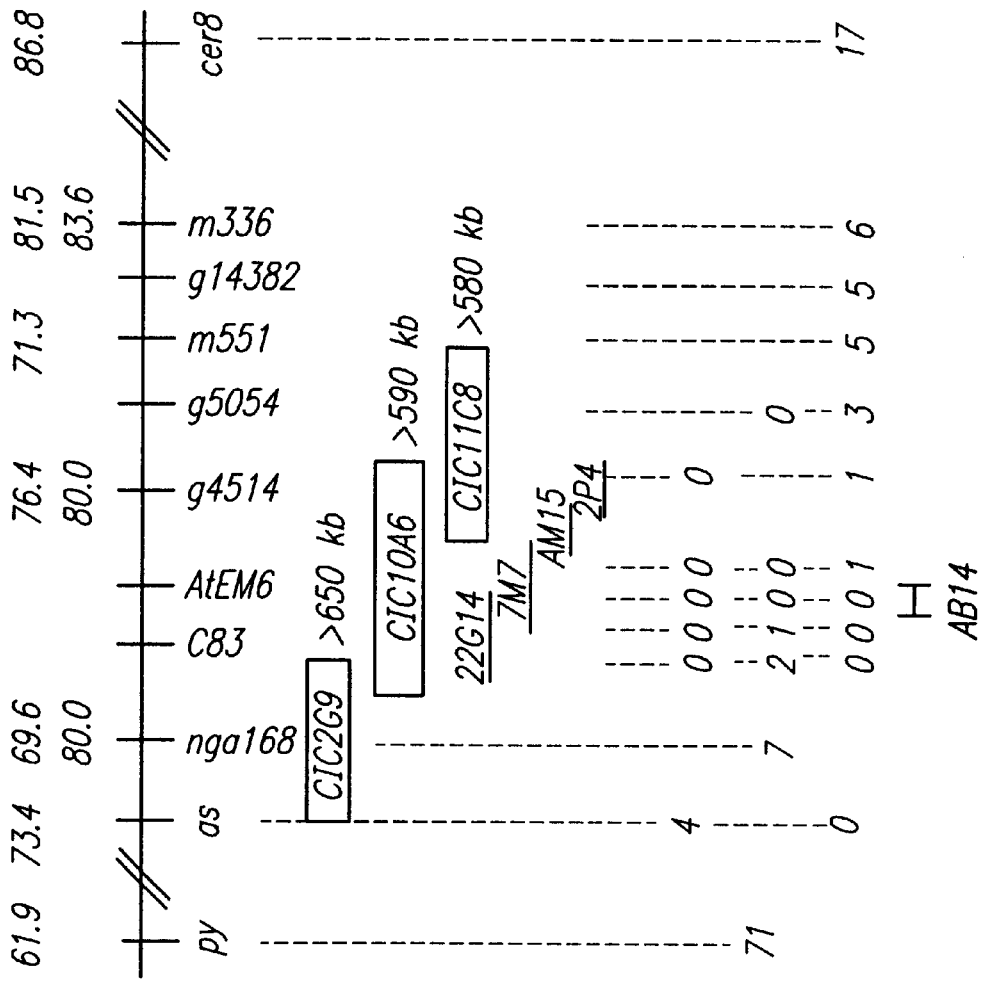
FIG. 1 shows fine-mapping of ABI4 on chromosome 2.

As used herein:

"ABI4" means an Arabidopsis gene required for normal response to abscisic acid.

"ABI4" means the protein encoded by the Arabidopsis ABI4 locus.

"abi4" means a mutant allele of the ABI4 gene comprising a single base pair deletion. Mutant seeds germinate on concentrations of ABA that would inhibit germination of wild-type seeds. In addition, abi4 mutants have altered expression of many genes expressed during embryogenesis and some ABA-regulated genes expressed in seedlings.

"APETALA" means gene(s) required for normal flower development; loss of function results in a variety of defects, including failure to produce petals.

"AP2" means APETALA2 protein, a DNA-binding protein that regulates expression of genes required during flower development.

"AP2 domain" means conserved region of a family of transcription factors, believed to function in DNA-binding and protein-protein interactions.

"ABA" means abscisic acid.

"ABI" means ABA-insensitive and refers to gene(s) required for normal ABA response.

"BAC" means bacterial artificial chromosome.

"RFLP" means restriction fragment length polymorphism, a type of molecular marker used for genetic mapping analysis.

"CAPS" means cleaved amplified polymorphic sequences, a type of molecular marker used for genetic mapping analysis.

"ABRC" means Arabidopsis Biological Resources Center.

"YAC" means yeast artificial chromosome.

"SSLP" means short sequence length polymorphism, a type of molecular marker used for genetic mapping analysis.

"Silique" means seed pod plus enclosed seeds and embryos.

"COL" means Columbia ecotype inbred line of Arabidopsis.

DETAILED DESCRIPTION OF THE INVENTION

This invention is based on findings that Arabidopsis abscisic acid-insensitive abi4 mutants have pleiotropic defects in seed development, including decreased sensitivity to ABA-inhibition of germination and altered seed-specific gene expression. The Arabidopsis abi4 phenotype is consistent with the discovery that ABI4 regulates seed responses to ABA and/or seed-specific signals. ABI4 has been found to be expressed at a low level in vegetative tissue, where it is required for full ABA-induction of some genes correlated with desiccation tolerance. The abi4 mutation also alters vegetative ABA responses that are dependent on ectopic ABI3 expression, providing further evidence that ABI4 plays a role in vegetative growth.

I. Arabidopsis ABI4 Gene

The ABI4 gene, unlike ABI3 gene, is expressed in both seed and vegetative tissues. The ABI4 gene regulates or is involved in regulation of seed properties. By over- or under-expression of the ABI4 gene, the properties of the seed may be regulated and modified. Modifying ABI4 expression in vegetative tissue will also alter ABA-sensitivity.

The ABI4 gene has now been identified by mutation, isolated by positional cloning, sequenced and its identity confirmed by complementation. The predicted protein product shows homology to a plant-specific class of transcriptional regulators characterized by a conserved DNA-binding domain, the AP2-domain. Based on sequence comparisons with other AP2-domain genes, the ABI4 gene appears to be the sole member of its Arabidopsis subfamily, with homology limited to the conserved DNA-binding domain. The single mutant allele identified to date has a single base pair deletion, resulting in a frameshift that disrupts the C-terminal half of the protein but leaves intact the domain presumed to bind DNA.

The abi4 mutant, which is a defective ABI4 gene and has altered ABI4 gene properties, was isolated in an effort to identify genes required for ABA regulation of seed quality and vegetative growth. Initial genetic and physiological characterization of the mutant indicated that the ABI4 gene primarily affected seed development and was likely to be acting in the same signaling pathway as the ABI3 gene.

In order to test the predictions based on the genetic evidence and potentially manipulate ABI4 expression, it was necessary to clone the gene and identify its protein product. Because there were no "tagged" alleles, that is, mutations created by insertions of known DNA sequences, and information regarding the likely biochemical product was not available, a positional cloning approach to identify the ABI4 gene was used. Using markers previously placed on the physical and genetic maps of chromosome 2, such as markers described in Genomics, 19:137–144 (1994), Plant Journal, 10: 733–736 (1996); and Genome Research, 6: 19–25 (1996), the ABI4 gene was localized within a single yeast artificial chromosome (YAC).

New restriction fragment length polymorphism (RFLP) markers to map the gene within a bacterial artificial chromosome (BAC) contig underlying the YAC were generated according to Plant Journal, 12:711–730 (1997). While confirmation of the ABI4 gene's identity relied on functional evidence from complementation data, initial identification of candidate genes depended on large-scale sequencing and sequence analysis.

A. Fine-Mapping of ABI4

Fine-mapping of the ABI4 gene on chromosome 2 utilized a positional cloning technique.

Positional cloning is a means of identifying the smallest possible region of DNA that could contain a specific gene. The technique relies on the principle that, when homologous chromatids pair during meiosis (leading to gamete formation), regions along a chromosome that are very close together or are tightly linked will recombine very rarely relative to those that are more distantly spaced. A series of molecular markers that detect minor differences in DNA sequence between the parental lines used in mapping crosses are used to identify specific DNA fragments that are very closely linked to the target locus and thus show minimal recombination.

Initial mapping of the ABI4 gene localized the gene to the lower arm of chromosome 2, very near the short sequence length polymorphism (SSLP) marker nga168. In order to generate fine-mapping populations with closely linked recombinations, the abi4 mutant in the Columbia (Col) ecotype background was outcrossed to lines containing the er and py or cer8 mutations in the Landsberg (Ler) ecotype background and screened for recombinants with these visibly scorable markers.

Recombinant families were subsequently scored at a series of molecular markers to identify the region of chromosome 2 that was most tightly linked to the ABI4 gene. This enabled fine-mapping of ABI4 to within a single BAC, TAMU7M7, as seen in FIG. 1.

FIG. 1 shows fine-mapping of abi4 on chromosome 2. For the fine-mapping, 92 recombinants across a 25 centimorgan (cM) interval, corresponding to at least 5 Mega-base pairs of DNA, surrounding abi4 were isolated. Results of mapping with a series of molecular markers across the interval are summarized schematically in FIG. 1, indicating that the closest recombinations are located within a single BAC containing approximately $10^5$ bp of DNA, representing less than a 1 cM interval. FIG. 1 also shows the map positions of molecular markers included on the recombinant inbred (RI) genetic map.

The BAC obtained above was sequenced and the genes, predicted by GRAIL analysis, according to Genomics, 24:135–136 (1994), were used to search available sequence databases. The closest recombinations in the available mapping populations were nearly 60 kb apart and the intervening DNA contained 12 predicted genes seen in FIG. 2. These predicted genes included AtEm6 (a late embryognesis abundant gene previously shown to have altered expression in the abi4 mutant), an ABI1/ABI2 homolog, and two probable transcriptional regulators, one representative each of the MADS- and AP2-domain families. Transcript levels for the ABI1/ABI2 homolog and presumed transcriptional regulators in wild type vs. abi4 siliques were then compared and it was found that one of these, corresponding to gene 10, showed a severely altered transcript accumulation in mutant siliques, leading to focusing attention on this gene.

The ABI4 gene has been fine-mapped to a 60 kb region of chromosome 2 contained within a single BAC, TAMU7M7. Out of 12 predicted genes within this interval, the one most likely to be the ABI4 gene encoded a likely regulatory protein whose expression was reduced in the abi4 mutant.

B. Identification of the ABI4 Gene

After fine-mapping of the ABI4 gene, the further experiments were directed to identification of the ABI4 gene on the basis of gene function.

Figure 2:
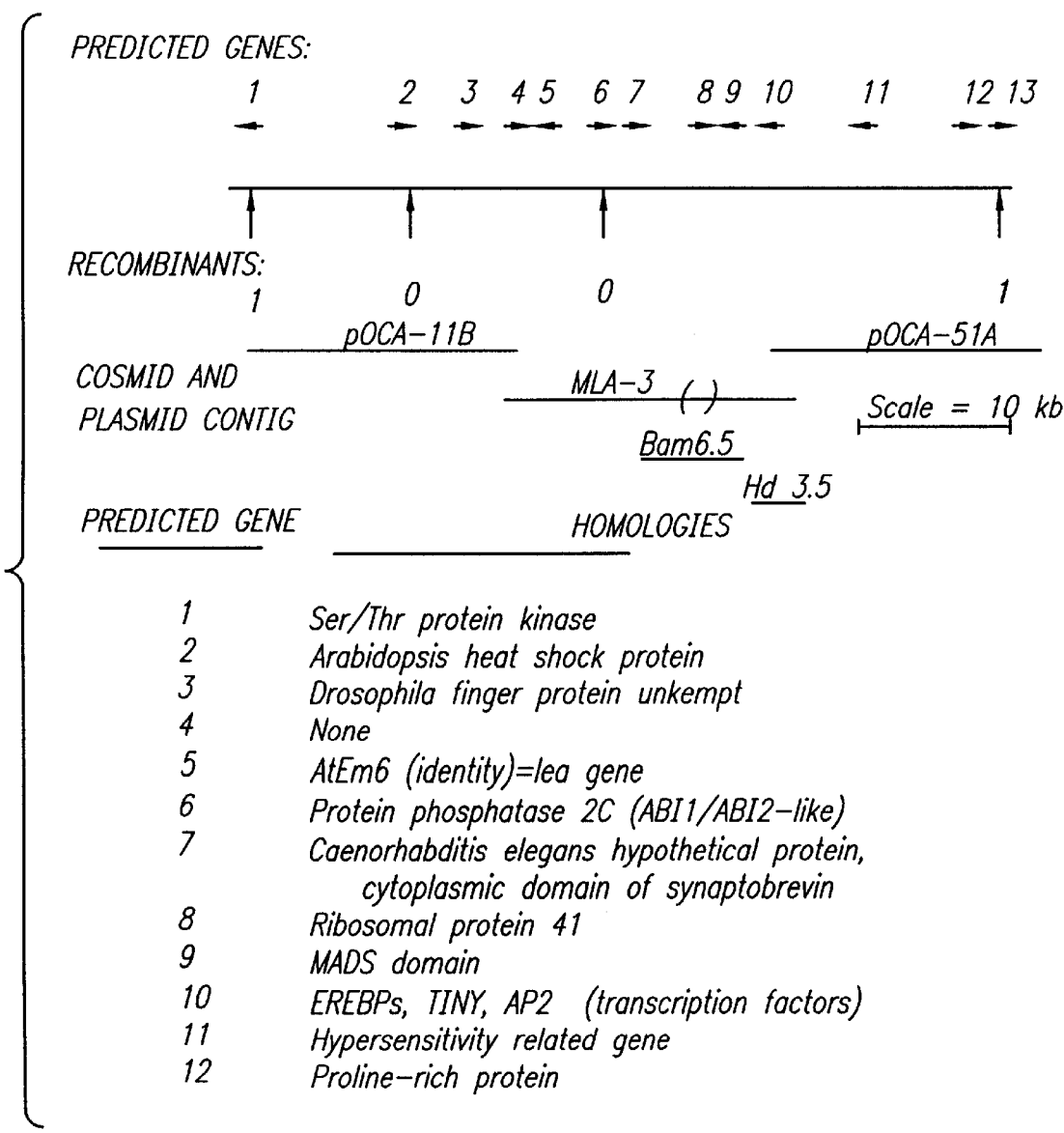
FIG. 2 shows genomic organization of the region between the closest flanking recombinant markers.

For identification of the ABI4 gene, a set of overlapping cosmid and plasmid constructs (pOCA-11B, pOCA-51A, MLA-3, Bam6.5, and Hd3.5) derived from wild-type DNA that spanned the region between the two closest recombinations, as seen in FIG. 2, was assembled and introduced into abi4 mutant plants by Agrobacterium-mediated transformation. The DNA segment containing the wild-type version of the ABI4 gene provides the information missing in the mutant, thereby rescuing or complementing it by restoring normal ABA responsiveness.

FIG. 2 shows the genomic organization of the 60 kb of BAC TAMU7M7 between the closest flanking recombinant markers. vertical arrows indicate sites of polymorphisms scored by RFLPs or cleaved amplified polymorphic sequences (CAPS). Predicted genes and their homologies are indicated, with arrowheads indicating the presumed direction of transcription. Predicted exon/intron structures of individual genes are not depicted. The cosmid and plasmid contig illustrates the extent of constructs used in complementation experiments. The parenthesis by clone MLA-3 indicate a small deletion in this clone.

To test for complementation by the transgene, seeds from individual kanamycin resistant T2 progeny were assayed for ABA sensitivity. The same seed lots were tested for kanamycin resistance, to determine whether each line was hemi- or homozygous for the transgene. Results of these assays show that approximately 75% of the progeny of the hemizygous lines were kanamycin resistant, consistent with segregation of a single transgene locus. ABA sensitivity of homozygous T₃ lines is compared in Table 1.

TABLE 1

| Line[a] | Intact Genes Transferred | Kanamycin Resistance[a] | Germination on 5 μM ABA[b] |
|---|---|---|---|
| Col | n.a.[c] | n.a. | 11 ± 12% |
| abi4 | n.a. | n.a. | 93 ± 4% |
| Bam6.5 | 8 | 100% | 97% |
| MLA3-8 | 5,6,7,9,10 | 100% | 100% |
| MLA3-9 | 5,6,7,9,10 | 100% | 86 ± 8% |
| Hd3.5-1a | 10 | 100% | 16 ± 13% |
| Hd3.5-4c | 10 | 100% | 13% |
| Hd3.5-4d | 10 | 100% | 10 ± 1% |
| Hd3.5-6b | 10 | 100% | 13 ± 1% |
| Hd3.5-4a | 10 | 100% | 70 ± 33% |

(a) Kanamycin and ABA sensitivity in progeny of transgenic individuals selected by growth on kanamycin was compared with that of the progenitor abi4 line and the corresponding wild-type (Col).

(b) Plates were incubated 3–4 days at 4° C. after sowing seeds. Germination on ABA was scored after 5 days at 22° C. Kanamycin resistance was scored after 8–10 days. Germination percentages represent assays of seeds from individual transgenic plants. Averages are derived from assays of sibling homozygous progeny of individual transgenic lines.

(c) n.a.=not applicable.

Table 1 illustrates complementation of the abi4 mutation by transgenes. A construct transferring a 3.5 kb HindIII fragment containing only the gene whose transcript was altered in the mutant (gene 10), including 1.3 kb upstream of the coding sequence, was the only clone that complemented the mutation to restore ABA sensitivity such that germination on ABA was reduced to approximately wild-type levels. Surprisingly, the cosmid MLA-3 which contains the entire 3.5 kb HindIII fragment, an additional 1.7 kb upstream of gene 10 and intact copies of four other genes, did not complement the abi4 mutation. The apparent inconsistency in the abi4 mutation complementation indicates that the additional 1.7 kb of upstream sequence present in the MLA-3 cosmid negatively regulates gene 10 or that some sequences required for proper expression of gene 10 lie even further upstream.

Having determined that the only complementing predicted gene encoded a regulatory protein which was underexpressed in mutant tissue, the mutant allele was sequenced. A single bp deletion in the coding sequence was found, resulting in a frameshift and early translation termination. This deletion also destroys an NlaIV site, creating an RFLP between the mutant and its progenitor line and providing a simple means for testing whether the identified mutation is an artifact of the sequencing technique. The loss of this site was confirmed by Southern analysis of genomic DNA, seen in FIG. 3.

Figure 3:
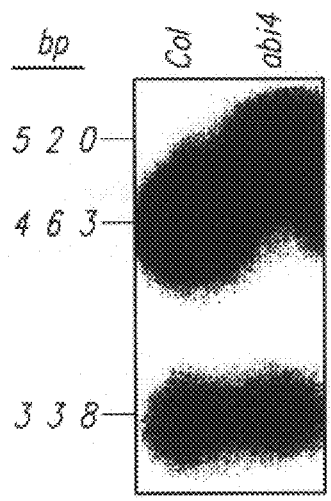
FIG. 3 shows a restriction fragment length polymorphism (RFLP) due to a deletion in the abi4 mutant.

FIG. 3 presents a DNA gel blot comparison of wild-type and mutant genomic DNA. Genomic DNAs were digested with NlaIV, then subjected to Southern hybridization analysis. The single base pair deletion detected by sequence analysis was located at position 468 of the coding sequence and was predicted to destroy an NlaIV site in the mutant, creating an NlaIV RFLP. Numbers on the left side of the gel indicate the length of the NlaIV fragments detected by the ABI4 probe. The presence of a 520 bp fragment in the abi4 mutant DNA, instead of the 463 bp fragment present in wild-type DNA, confirms the predicted loss of the NlaIV site.

The abi4 mutation thus comprises a single base pair deletion responsible for the modified function of the expressed ABI4 protein, resulting in the altered seed properties of the abi4 mutant. The combination of an identified sequence mutation and the functional evidence from complementation indicate that this gene is indeed ABI4.

C. Homology of ABI4 to AP2-Domain Proteins

A region of the protein encoded by the ABI4 gene is highly homologous to other known transcription factors.

Analysis of the ABI4 genomic sequences and domain structure of the ABI4 protein is shown in FIG. 4.

FIG. 4A shows the DNA sequence of the genomic region including the ABI4 coding sequence (SEQ ID NO: 1) deposited at GenBank under Accession# AF040959. The predicted amino acid sequence (SEQ ID NO: 2) of the single open reading frame in the ABI4 gene is shown below the DNA sequence. The stop codon is marked with an asterisk. The location of the single bp deletion in the abi4 mutant (SEQ ID NO: 3) is indicated by a Δ. The double underlined region shows homology with other AP2-domain genes, as illustrated in FIG. 5. Putative nuclear localization signals are bold-faced. Sites of polyadenylation in 3 independent cDNAs are indicated by carets "^" symbols.

FIG. 4B is a schematic diagram of the predicted ABI4 protein, showing locations of the AP2-domain, basic region, putative dimerization domain, and serine/threonine-rich, glutamine-rich, proline-rich and acidic domains.

As seen in FIG. 4, analysis of the ABI4 genomic sequence predicts a 1.3–1.5 kb transcript comprised of a single exon. Although no full-length ABI4 cDNAs were obtained from either silique-specific or mixed stage and tissue cDNA libraries (*Plant Physiology*, 106: 1241–1255 (1994)), the predicted structure is consistent with the sequence of cDNA clones obtained by the 3'RACE technique (*PCR Primer, A Laboratory Manual*, 381–409, C. W. Dieffanbach, G. S. Dveksler, Eds., Cold Spring Harbor Laboratory Press, Plainview, N.Y., (1995)).

The 3'ends of these clones were found to be somewhat heterogeneous, indicating that any of several possible polyadenylation signals can be used. Comparison of the ABI4 sequence with other genes in databases shows greatest homology with those encoding a class of proteins including tobacco ethylene response element binding proteins (EREBPs) (*Plant Cell*, 7: 173–182, 1995), the Arabidopsis TINY protein (*Plant Cell*, 8: 659–671, 1996), the Arabidopsis CBF1 protein (*PNAS (USA)*, 94:1035–1040, (1997)) a cadmium-induced protein isolog (predicted protein from unpublished BAC sequence TO1B08.3) and a limited stretch (residues 55–98) of high homology to the APETALA2 (AP2) protein (*Plant Cell*, 6: 1211–1225, 1994).

While overall similarity of the ABI4 protein with the closest homolog is only 30%, the conserved region is 70% similar, as seen in FIG. 5. FIG. 5 shows homology between ABI4 (SEQ ID NO: 4) and other AP2-domain proteins by comparison of the conserved regions of ABI4 and other AP2-domain proteins. Accession numbers for these genes are provided in brackets following the gene names: CBFI (U77378) (SEQ ID NO: 5), TINY (X94698) (SEQ ID NO: 8), EREBP1 (D38123) (SEQ ID NO: 9), AtEBP (Y09942) (SEQ ID NO: 10), Lpplzp2 (X51767) (SEQ ID NO: 6), and AtCdinp (Z37504) (SEQ ID NO: 7). Ap2r1 (SEQ ID NO: 11) and Ap2r2 (SEQ ID NO: 12) correspond to two repeats of the AP2 domain within the AP2 protein. Amino acids identical to the ABI4 sequence are designated by asterisk "^". Gaps in the sequence are indicated by dots. The consensus sequence for the EREBP-like subfamily (*PNAS* (*USA*), 94:7076–7081 (1997)) is shown below, with invariant residues capitalized, conserved residues in lower case, and positions that usually contain positively charged residues indicated as plus signs.

The conserved region of the ABI4 gene corresponds to the AP2 domain which is believed to be involved in DNA-binding and potential dimerization of this class of transcription factors. This supports the current findings that ABI4 is involved in regulation of seed properties probably as a transcription factor.

In addition to the conserved AP2-domain, the sequence has several characteristics consistent with function as a transcription factor. These include the presence of a serine/threonine-rich domain (73% over 30 amino acids, residues 111–140) and a glutamine-rich domain (62% over 21 amino acids, residues 188–208). Less striking than the glutamine-rich domain, but possibly also relevant for transcriptional activation are the proline-rich domain (33% over 15 amino acids, residues 275–289) and acidic domain (22% over 32 amino acids, residues 295–326). The abi4 mutant lacks these domains.

The predicted ABI4 gene product protein has two lysine/arginine rich regions, located at residues 40–45 and 74–79, seen in FIG. 4A, that might function as nuclear localization signals. Although one of these regions falls within a basic region of the AP2-domain that might be involved in DNA binding, this is a region of low homology among AP2-domain proteins. Furthermore, many proteins have overlapping DNA-binding and nuclear localization domains.

The site of the abi4 mutation is indicated by a "Δ" as seen in FIG. 4B. The abi4 mutant allele encodes complete presumed DNA-binding, dimerization and nuclear localization domains, but lacks the glutamine-rich, proline-rich, and acidic domains, which are most likely to function in transcription activation.

Differences between the nucleotide sequence of the wild-type ABI4 gene and the abi4 mutant gene clearly demonstrate that the mutated abi4 gene is responsible for loss of function of this transcriptional factor regulating desirable seed properties.

D. ABI4 Gene—A Member of A Gene Family

To determine whether ABT4 is likely to have more closely related family members than those represented in the sequence databases, ABI4 DNA was used as a probe in reduced stringency Southern hybridizations of genomic DNA.

FIG. 6 shows that ABI4 is a member of a small gene subfamily. In FIG. 6, genomic Arabidopsis DNA was cleaved with BamHI, EcoRI or EcoRV, then subjected to Southern hybridization analysis at a variety of stringencies. In panels seen in FIGS. 6A–C, the probe was a 524 bp fragment encoding residues 3–176, including the AP2-domain, residues 55–98. In panel D, FIG. 6, the probe was a 492 bp fragment encoding residues 161–324.

Figure 6A:
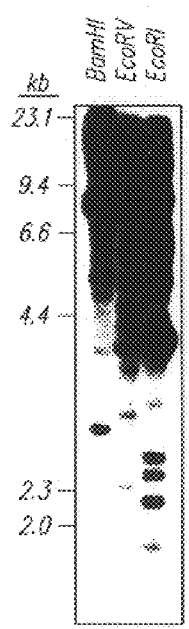
FIG. 6(A–D) shows DNA gel blot hybridization analysis of the ABI4 gene at various stringencies.
Figure 6B:
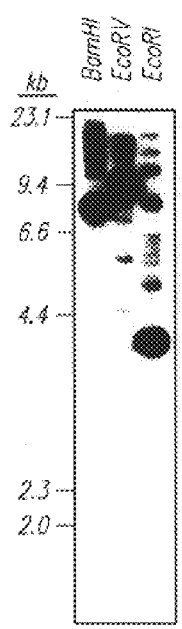
Figure 6C:
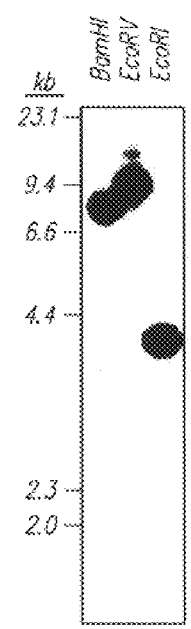
Figure 6D:
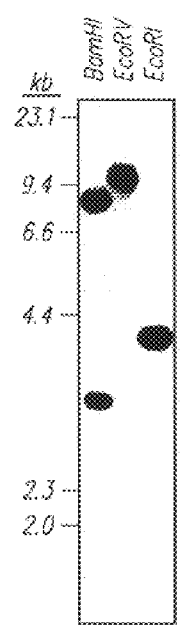

Hybridization conditions were as follows: In FIG. 6A, a filter was hybridized at 45° C. in 5×SSPE, 35% formamide, 5×Denhardt's solution, 0.5% SDS and 200 ug/ml herring testes DNA, then washed at 50° C. in 0.2×SSC, 0.1% SDS. In FIG. 6B, the same filter was rewashed at 55° C. In FIG. 6C, the same filter was rewashed at 60° C. In FIG. 6D, hybridization and wash conditions were the same as for FIG. 6A, but the probe corresponded to the 3' end of the gene.

As shown in FIG. 6, hybridization to the ABI4 gene itself produces the prominent bands corresponding to fragment sizes of 7.9, 9.5 and 4 kb in the BamHI, EcoRV and EcoRI digests, respectively. The lighter bands, which disappear as the wash temperature increases, are due to imperfect hybridization to related sequences. This experiment demonstrated that there are at least ten related sequences, as seen in FIG. 6A, several of which are quite closely related, as seen in FIGS. 6B and 6C. When hybridized at comparable stringencies to a probe corresponding to the 3' 40% of the coding sequence, thereby excluding the AP2-domain encoding region, this gene appears to have no close homologs, as shown in FIG. 6D. The novel 3.2-kb Bam fragment detected by the 3' probe reflects the fact that this fragment spans a Bam site not present in the other probe. These results show that standard hybridization conditions used in the expression studies described below in FIGS. 7 and 8 are selective for the ABI4 gene.

The fact that the 3' 40% of the coding sequence hybridizes only to ABI4 indicates that, although ABI4 is a member of the AP2-domain protein family, it appears to be a unique member of its own subfamily.

E. ABI4 Expression

As described above, initial genetic and physiological studies showed that ABI4 expression was likely to be seed-specific in wild-type plants.

To test the specificity of ABI4 expression, ABI4 transcript levels in developing siliques vs. vegetative tissue were compared. Results are seen in FIG. 7.

FIG. 7 shows gel blot analysis of RNA extracted from the indicated tissues of flowers, shoots, roots, and wild-type (Col) and mutant (abi4) siliques. Each lane contains 25 µg total RNA. Uniformity of loading and transfer was confirmed by methylene blue staining.

Figure 7A:
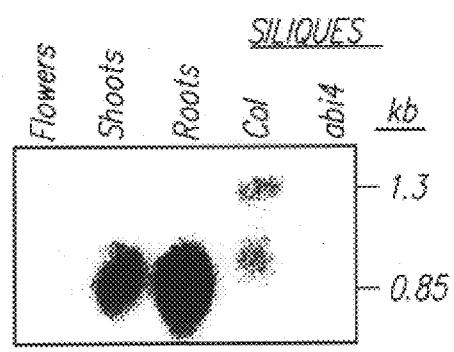
FIG. 7A shows hybridization with the fragment including the AP2 domain coding region.
Figure 7B:
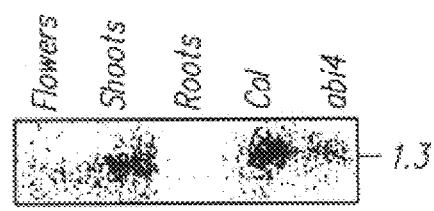
FIG. 7B shows hybridization with the fragment corresponding to the 3' portion of the gene.
Figure 8:
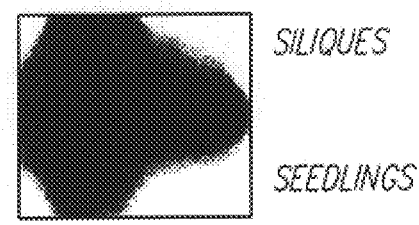
FIG. 8 shows full length cDNAs amplified from silique and seedling RNA, detected by Southern hybridization of 3'RACE products.

FIG. 7A shows hybridization to the fragment including the AP2-domain coding region. FIG. 7B shows hybridization to the fragment corresponding to the 3' portion of the gene. Length of the observed transcripts are indicated as kb on the right side of the gels.

As seen in FIG. 7A, a 1.3 kb transcript was detected in wild-type siliques, but was absent or greatly reduced in abi4 siliques and wild-type vegetative tissue. Additional hybridization was observed at approximately 1 kb in silique RNAs. However, a more abundant smaller transcript of approximately 850 nucleotides was present in roots and shoots of 3 week old plants. None of these transcripts accumulated to detectable levels in flowers, but preliminary studies with ABI4::β-glucuronidase transgenic lines show transient β-glucuronidase activity in immature anthers. This is consistent with a role for ABI4 in regulating gene expression, such as production of desiccation protectants, in maturing pollen as well as maturing seeds.

The accumulation of smaller transcripts was especially surprising because the gene appears to lack introns and is therefore not a good candidate for alternative splicing. To determine whether the small transcripts were derived from the ABI4 gene, RNA blots were hybridized with a probe corresponding to approximately 0.5 kb of the 3' portion of the gene, excluding the conserved AP2 domain. The smaller transcripts did not contain this region, but low levels of the full-length transcripts were detected in vegetative shoots, seen in FIG. 7B.

To amplify any ABI4 products from the vegetative tissue, gene-specific primers annealing 30 nt upstream of the predicted start codon in 3'RACE reactions were again used. Results are seen in FIG. 8.

FIG. 8 shows full-length cDNAs amplified from silique and seedling RNA. 3'RACE products from amplification of first strand cDNA reverse transcribed from silique and seedling RNA were detected by Southern hybridization analysis. The probe was the 524 bp fragment encoding residues 3–176.

As shown in FIG. 8, no truncated products were obtained. Because 3'RACE depends on an oligo(dT) primer to target amplification of polyadenylated transcripts, the failure to amplify a truncated product indicates that the truncated transcripts are not polyadenylated. Consistent with this finding, the smaller transcripts were not observed in polyA+ RNA from silique tissue (data not shown). However, low levels of full length cDNAs were amplified from RNA isolated from 11 day old seedlings, indicating that the full-length ABI4 transcript is not absolutely seed-specific. This is consistent with a role for ABI4 in regulating ABA response of seedlings.

Although the RACE PCR conditions were not designed to support quantitative comparisons, the fact that significantly less product was derived from seedling cDNA amplification suggests that the correctly sized vegetative transcript was below the limit of detection on the initial Northern blots. The identity and origin of the smaller vegetative transcript is still unclear. This transcript might be a degradation product of the ABI4 transcript or it could be derived from a homologous family member divergent in or lacking the sequences present at the 3' end of ABI4.

RNA gel blot analyses of ABI4 expression showed that a full-length transcript accumulates primarily in seeds but also at much lower levels in seedlings.

F. The abi4 Mutation Suppresses the ABA Hypersensitivity Conferred by Ectopic Expression of ABI3

In order to further study interactions between the ABI3 and ABI4 loci, the effects of the abi4 mutation on the hypersensitivity to ABA conferred by ectopic ABI3 expression were examined.

The fact that ectopic ABI3 expression and the abi4 mutation have essentially opposite effects on ABA response permitted testing for epistatic relationships between these genes. These tests improved understanding of the relationship between ABI4 and ABI3 regulation and therefore the ability to predict and confirm effects of modified ABI4 expression.

Figure 9:
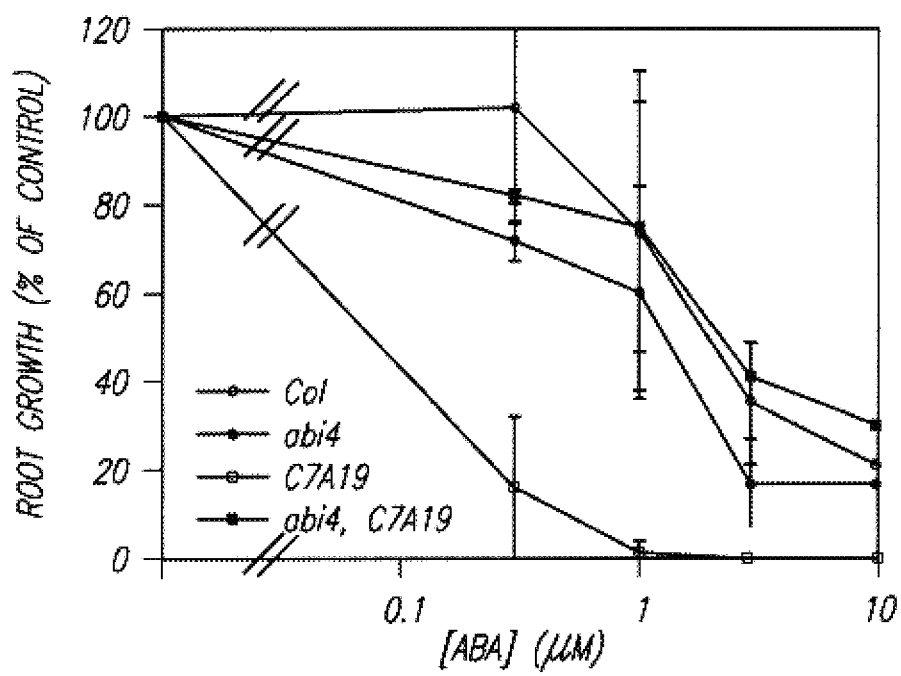
FIG. 9 shows that the abi4 mutation suppresses the hypersensitivity to ABA-inhibition of root growth resulting from ectopic ABI3 over-expression.

For these tests, both strongly and weakly expressing 2×35S::ABI3 transgenes (*Plant Cell*, 6:1567–1582 (1994)) were crossed into the abi4 mutant background. As described in Example 11, progeny homozygous for both the transgene and the abi4 mutation were identified by linked markers: kanamycin resistance and the py mutation, respectively. The lines carrying both the abi4 mutation and a 2×35S::ABI3 transgene were compared with the original transgenic lines and the wild type and abi4 mutant parents in terms of sensitivity to ABA inhibition of root growth and ABA-inducible gene expression. Results of root growth assays are seen in FIG. 9. ABA-induction of seed-specific transcripts in vegetative tissue is seen in FIG. 10.

FIG. 9 illustrates the effects of a strongly expressed 2×35S::ABI3 transgene, seen in FIG. 9 as C7A19, compared with abi4, C7A19, and the abi4 mutation. In the case of root growth seen in FIG. 9, the abi4 mutation suppressed the ABA hypersensitivity conferred by the 2×35S::ABI3 transgene, consistent with an epistatic (downstream) effect of the abi4 mutation.

For the studies shown in FIG. 9, the procedure used is described in Example 12. Comparison of sensitivity to ABA-inhibition of root growth shows that, although the 2×35S::ABI3 line (C7A19) is at least thirty-fold more sensitive to ABA than wild-type (Col), the abi4 mutants have wild-type sensitivity to ABA regardless of whether the 2×35S::ABI3 transgene is present. This shows that the ABI3 transgene cannot confer ABA hypersensitivity in the absence of a functional ABI4 gene product.

Figure 10:
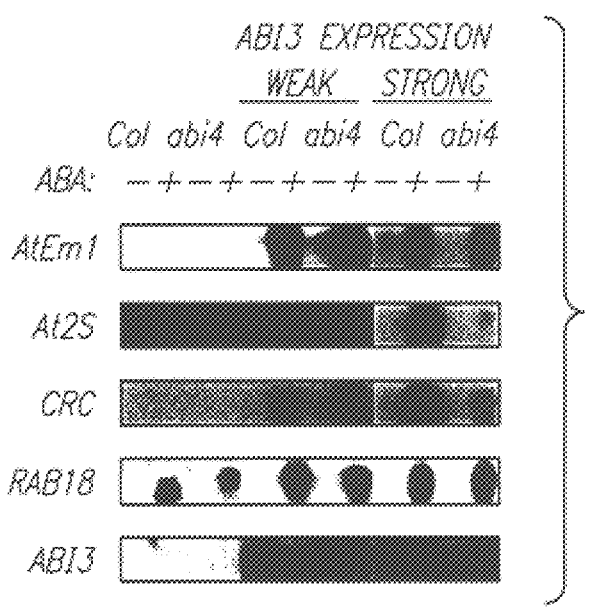
FIG. 10 shows that the abi4 mutation modulates ABA-induced, ABI3-dependent vegetative expression of seed-specific transcripts.

FIG. 10 shows that the abi4 mutation modulates ABA-induced, ABI3-dependent vegetative expression of seed-specific transcripts.

For the studies shown in FIG. 10, the procedure used is described in Example 13. RNA was extracted from 11 day old seedlings incubated for 2 days on plates in the presence or absence of 50 uM ABA, then analyzed by Northern blots hybridized to cDNA clones for AtEm1, At2S, CRC, RAB18 and ABI3. Six genotypes were compared: Col and abi4 with no (left), weakly (middle), and strongly (right) expressed 2×35S::ABI3 transgenes.

The effects on vegetative expression of the normally seed-specific genes, as seen in FIG. 10, were complex. Some transcripts (CRC and At2S) were either over- or under-induced relative to the original transgenic line, depending on whether the transgene was weakly or strongly expressed. Other transcripts that are normally only weakly induced by ABA in seedlings (AtEm1 and RAB18) showed reduced ABA-induction in the abi4 mutant, but the higher level of ABA-induction due to the 2×35S::ABI3 transgene was unaffected by the abi4 mutation.

Although the relationship between ABI3 and ABI4 is not clear in this situation, the abi4 mutation clearly modifies the effects of the transgene. These results, along with the reduced ABA-inducibility of AtEm1 and RAB18 in the abi4 mutant, show that the low level of ABI4 expression in vegetative tissue is functionally relevant.

G. Effects of ABI4 Ectopic Expression

To determine whether altered ABI4 expression is sufficient to modify ABA sensitivity of various plant tissues, a 35S::ABI4 fusion gene was created by cloning the ABI4 coding sequence downstream of the CaMV35S promoter present in the vector pGA643 (*Plant Molecular Biology Manual*, A3: pp. 1–19, S. B. Gelvin and R. A. Schilperoort, Eds., Kluwer Academic Publishers, pp. 1–19 (1988)).

The 35S::ABI4 fusion gene was then introduced into wild-type Arabidopsis plants by Agrobacterium mediated transformation. Plants homozygous for the transgene were selected on the basis of kanamycin resistance conferred by neomycin phosphotransferase II (NPTII), the selectable marker present adjacent to the cloning site in the pGA643 vector.

Figure 11A:
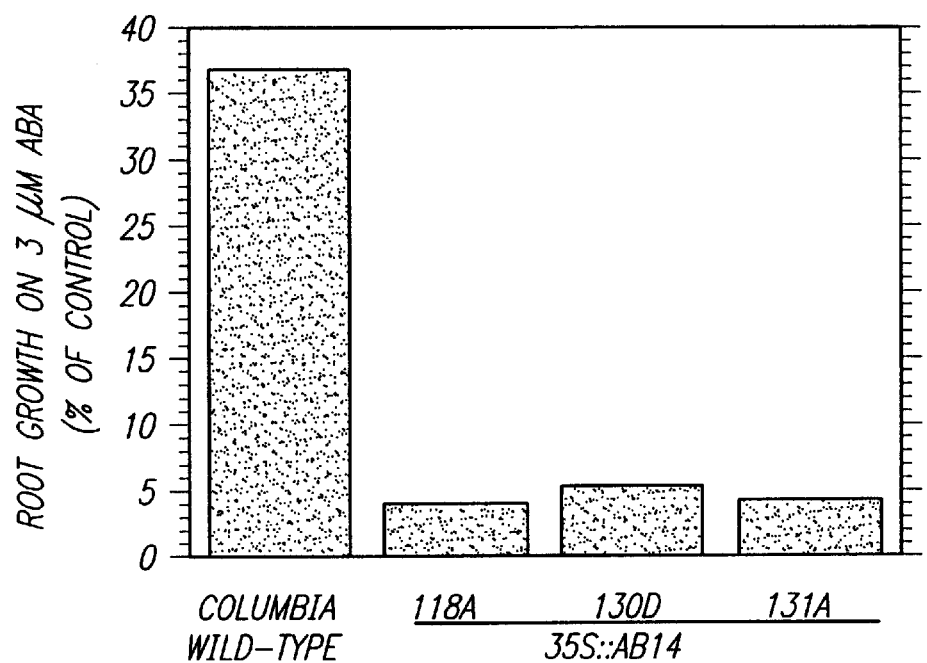
FIG. 11A shows sensitivity of root growth inhibition by ABA in ABI4 ectopic expression lines.
Figure 11B:
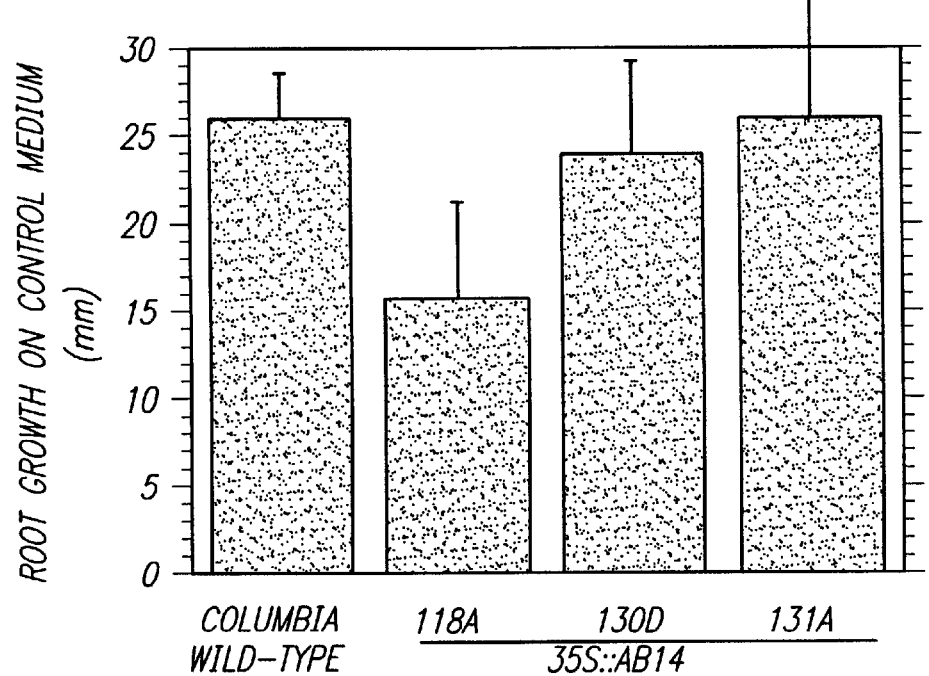
FIG. 11B shows root growth on control media.

Several independent transformed lines have been tested for altered ABA sensitivity of root growth and vegetative gene expression. Results of the root growth assays are shown in FIG. 11. For studies shown in FIG. 11, the procedure used is described in Example 12. FIG. 11A shows root growth in the presence of 3 uM ABA as a percentage of growth on hormone-free medium, while FIG. 11B displays growth on control media.

FIG. 11 illustrates that ectopic expression of ABI4 increases ABA sensitivity of root growth inhibition. All 35S::ABI4 lines tested to date are far more sensitive to ABA-inhibition of root growth than wild-type plants, as seen in FIG. 11A, but most grow normally in the absence of applied ABA, as seen in FIG. 11B.

Figure 12:
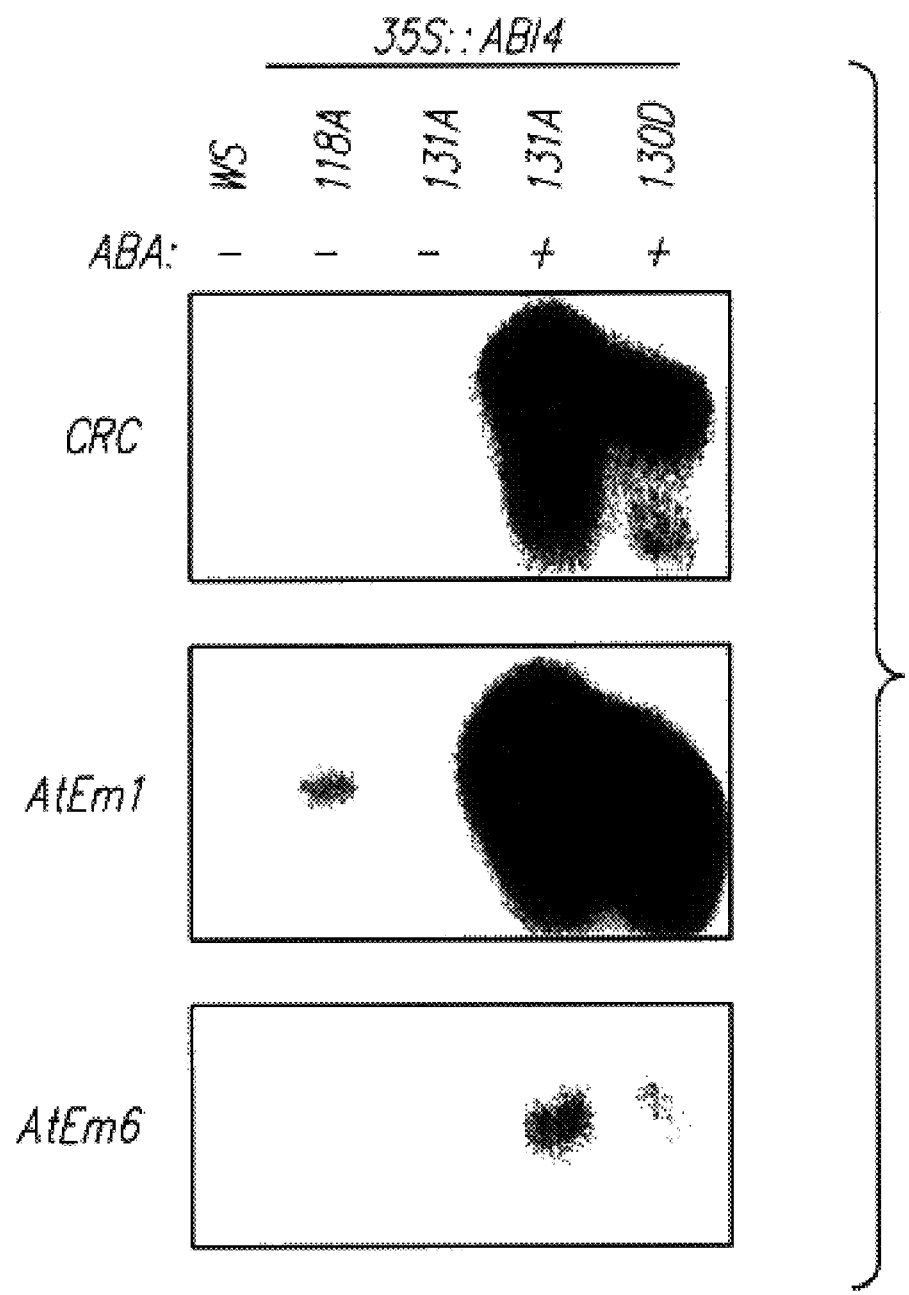
FIG. 12 shows that ABI4 ectopic expression confers vegetative ABA-inducibility on several seed-specific genes.

FIG. 12 compares vegetative expression of three seed-specific genes in a wild-type (WS) and three 35S::ABI4 lines. The procedure used for studies seen in FIG. 12 is described in Example 13. RNA was extracted from 11 day old seedlings of two 35S::ABI4 lines (131A and 130D) incubated for 2 days on plates in the presence or absence of 50 uM ABA, then analyzed by Northern blots hybridized to DNA clones for AtEm1, AtEm6, and CRC. Both lines show at least some ABI4-dependent ABA-inducibility for all genes tested to date. The WS and 118A RNA on this gel were isolated from 3 week old soil-grown plants that had not been exposed to ABA. As seen by comparison of the first two lanes in FIG. 12, increased ABI4 expression results in increased accumulation of at least one of these transcripts, AtEm1, even in the absence of applied ABA. Compared to the 2×35S::ABI3 transgenic lines (*Plant Cell*, 6:1567–1582 (1994)), increased ABI4 expression confers vegetative ABA-inducibility to an even larger number of otherwise seed-specific genes such as, for example, AtEm6, one of those presumed to be involved in desiccation tolerance.

Ectopic expression of ABI4 can thus result in accumulation of seed storage reserves and desiccation protectants in vegetative tissue exposed to ABA. Such exposure would occur under conditions of mild drought stress, at which time the desiccation protectants can enhance survival during continued stress conditions.

II. Properties of ABI4 Gene

The role of the ABI4 gene in ABA-inducibility and signaling has been analyzed by biochemical and genetic approaches.

The positional cloning of ABI4 has identified a protein class required for normal ABA response in seeds. ABI4 contains relatively small acidic and proline-rich domains, as well as a glutamine-rich domain. Any of these domains may function and be involved in transcription activation. The unique aspects of ABI4 are reflected in the gene-specific hybridization pattern of a probe spanning coding regions excluding the AP2 domain.

The full-length ABI4 transcript is more abundant in developing siliques than in seedlings, but is not absolutely seed-specific. This finding was surprising because initial phenotypic characterization of the abi4 mutant suggested that ABI4 action was necessary only during seed development. However, recent studies of ABA-regulated gene expression in seedlings show that ABI4 also plays a previously undetected role in vegetative growth.

The abi4 mutant allele contains a frameshift within the coding sequence such that the presumed DNA-binding and dimerization regions of the AP2 domain are present in the mutant, but the glutamine-rich, proline-rich, and acidic domains likely to function in transcription activation are lost. If these potential transcription activation domains are not essential for ABI4 function, the abi4 mutant may be a leaky allele. Consistent with this, antisense expression of ABI4 slightly enhances the ABA resistance of the mutant, indicating that the mutant still retains some function. If only some of the ABI4 protein's functions are lost in the available mutant, the mutant phenotype provides only a minimal estimate of the importance of ABI4 in regulating plant growth.

III. Method for Modification of Seed and Plant Viability and Stress-Tolerance A method for modification of seed and plant quality, viability and stress-tolerance comprises regulation of altered expression of the ABI4 gene, with the specific alteration depending on the desired end product. Such method is valuable for modification of a wide variety of crop plants, especially those species susceptible to pre-harvest sprouting or those normally grown in heavily irrigated arid environments or in regions subject to sporadic drought stress. Some examples of such crops include dicots, such as soybeans or cotton, and monocots, such as barley, wheat and other cereal grains.

The method generally comprises the following steps:
constructing an ABI4 transgene;
transferring the transgene into recipient plant; and
selecting and characterizing a transgenic individual.

The ABI4 transgene typically is constructed by fusing ABI4 coding sequence to a regulatory sequence for overexpression in embryos or shoots. Such regulatory sequence is either a promoter or a fragment acting as a transcriptional enhancer. Typically, the promoter is selected from the group consisting of late embryogenesis abundant genes, such as the Em genes, or highly expressed light regulated genes, such as the rbcS or cab genes. The fragment is typically selected from a group consisting of the cis-acting sequences demonstrated to be required for embryonic, ABA-regulated or light-regulated expression, such as the ACGT or RY repeat motifs.

The transgene is then transferred into recipient plant by Agrobacterium-mediated transformation, biolistic transformation, or electroporation.

The selection and characterization of the transgenic individuals is performed on homozygous transgenic individuals selected from primary transformant lines identified by scoring antibiotic or herbicide resistance. The antibiotic resistance is scored against kanamycin, neomycin, streptomycin, hygromycin, etc. Herbicide resistance is scored against herbicides such as BASTA or chlorsulfuron.

The method provides seeds, plants or cultivars with an enhanced resistance to drought, salt or cold stress, and with an extended storage stability.

Step 1 involves construction of an ABI4 transgene controlled by appropriate regulatory sequences.

The choice of regulatory sequences and vectors depends on the characteristics to be modified and the intended recipient species. A variety of selectable markers have been developed that confer resistance to antibiotics, such as hygromycin, streptomycin, kanamycin, neomycin, or G-418. Alternatively, genes conferring resistance to herbicides, such as BASTA or chlorsulfuron, may be used. The efficacy of these selections varies among plant species and cultivars. The selection strategy and corresponding cloning vector which is chosen depends and is determined by the intended recipient plant species. Regulatory sequences include promoters and/or fragments acting as transcriptional enhancers. The efficiency of expression in monocots can also be improved by inclusion of some intron sequences, such as the first intron of the maize Shrunken1 gene (*Plant Physiol.* 91:1575–1579 (1989)).

To limit pre-harvest sprouting and enhance seed viability, enhanced embryonic expression is, for example, achieved by fusing promoters from late embryogenesis abundant genes, or fragments thereof, to an ABI4 cDNA, similar to the construction described in Example 14.

Many such promoters have been well characterized and both monomers and multimers of cis-acting regions, such as the Em1a region of the maize Em gene, are known to function well as enhancers of ABA-responsive embryonic expression (*Plant Hormones: Physiology, Biochemistry and Molecular Biology*, 2nd ed., P. J. Davies, Ed., Norwell, Mass., Kluwer Academic Publisher, 671–697 (1995)). All functionally suitable promoters and cis-acting regions are intended to be within a scope of the invention.

For example, for efficient ABA-responsive embryonic expression, oligonucleotide primers to amplify a fragment of the Em promoter containing the Em1a/b regions are designed as described in *Plant Cell* 1:969–976 (1989). Individual or multimeric copies of this fragment are ligated into an EcoRV site approximately 0.5 kb upstream of the ABI4 coding sequence to drive enhanced ABI4 expression. The chimeric promoter-ABI4 fusion are then subcloned into appropriate site(s) in a vector, such as pBIN19 (*Nucleic Acid Res.*, 12: 8711–8721 (1984)), a T-DNA binary vector which contains a multiple cloning site region adjacent to a selectable marker, NPTII, in the T-DNA region.

Alternatively, a 1.3 kb EcoRI-PvuII fragment of the AtEm6 promoter are used which have approximately 40–120 bp deleted from the PvuII end, by either exonuclease deletion or PCR amplification of the smaller fragment. This fragment is used to create a transcriptional fusion with an ABI4 cDNA, similar to the construction described in Example 14. Because ABI4 regulates AtEm6 expression, this creates a strong positive feedback loop driving ABI4 expression in the late embryogenesis.

To improve stress-tolerance during vegetative growth, it would be desirable to enhance ABA-induction of desiccation protectants without making root growth hypersensitive to ABA such that even mild stress results in poor root growth. Such stress-tolerance improvement is achieved, for example, by creating a fusion with a promoter normally expressed strongly only in shoots, such as those for genes encoding the small subunit of Rubisco (rbcS), the chlorophyll a/b binding protein (cab) and other light-regulated genes.

Step 2 involves transfer of the transgene into recipient plants.

The method of delivery of the transgene into recipient plan depends on the recipient species. Two major methods of plant transformation useful for such delivery are Agrobacterium-mediated transfer of genes cloned between the right and left border sequences of a T-DNA vector, and biolistic, i.e., microprojectile-mediated, delivery of naked DNA.

Effective transformation protocols have been developed for many major crops which are known in the art and many variations within these protocols are possible. For example, Agrobacterium-mediated transformation may involve a complex series of tissue culture steps to induce callus formation. Such Agrobacterium-mediated transformation includes steps of infecting the recipient plant with Agrobacteria, selecting transformed cells and regenerating whole plants that can set seed carrying the transgene(s). The optimal culture conditions for all of these steps are highly specific to individual cultivars and are known in the art. Alternatively, Agrobacterium-mediated transformation is achieved by simply dipping or vacuum-infiltrating plants in a bacterial culture, then screening their progeny for the appropriate antibiotic or herbicide resistance, as described in Example 7.

In the example described above, introducing a chimeric ABI4/Em promoter-ABI4 fusion via pBIN19, the fusion gene is first introduced into Agrobacterium tumefaciens by either direct transformation, as described in Example 14, electroporation according to the recommendations of the Gene Pulser II manufacturer (Bio-Rad) or using any other suitable method. Transformed Agrobacteria are selected by demanding growth on yeast extract-peptone media, as described in *Plant Molecular Biology Manual*, A3:1–19, S. B. Gelvin, R. A. Schilperoort, Eds., Dordrecht: Kluwer Academic Publishers, (1988), supplemented with approximately 50 ug/ml kanamycin. Optimal transformation techniques for each cultivar depend on the desired recipient and are known in the art. Recently, genotype-independent transformation-regeneration of maize, cotton and pine using Agrobacterium has been described (*Plant Physiol.*, 114 (3 SUPPL.):304 (1997)) and are exemplary of such transformation.

For those species recalcitrant to Agrobacterium-mediated transformation, such as most monocots, biolistic transformation using microprojectile-mediated delivery is an efficient alternative, again with many possible variations. References describing various biolistic transformation techniques include *Euphytica*, 95:269–294 (1997); *Mol. Biotechnol.*, 6:17–30 (1996); *Biotechnol. Advances*, 13:631–651 (1995); *Genes and Genetic Systems*, 72:63–69 (1997); *Austr. J. Plant Physiol.*, 25:39–44 (1998), among others.

Step 3 involves selection and characterization of transgenic individuals.

Regardless of the method used for delivery of a transgene, transgenic individuals must be selected from a pool of untransformed tissue. When using Agrobacterium-mediated transformation or biolistic transformation in combination with regeneration through tissue culture, transgenic tissue is selected early such that regenerated plants are likely to be at least hemizygous for a transgene and should produce seed segregating the transgene. In contrast, when using an infiltration technique, selection of transgenic tissue is delayed until after seed set and these primary transformant lines are often hemizygous for the transgene. In either case, characterization of the transgenic phenotype is performed on homozygous lines, which can be identified by scoring antibiotic or herbicide resistance in the selfed progeny of transformants, as described in Examples 1 and 7.

The details of the physiological characterization will depend on the desired characteristics. For example, seed quality can be assayed in terms of protein and lipid composition, depth of seed dormancy, and germinability after storage under suboptimal conditions such as temperatures above 25° C. or high relative humidity. Vegetative drought tolerance can be assayed by imposing drought stress by ceasing watering and comparing withering of transgenic ABI4 overexpressors and control plants. Substantial variation in transgene expression can be expected due to effects of integration at different chromosomal sites, so it is important to screen many transgenic individuals for a desirable phenotype with any class of transgene.

Finally, transgenic lines displaying a desirable phenotype must be tested in different environments to determine whether the modification is consistently effective.

IV. Utility of ABI4 Gene and Its Expressed Protein

Characterization of the predicted ABI4 gene product and the phenotypic effects of the abi4 mutation has provided evidence of effects of modified ABI4 expression. Reduced ABI4 function, as seen in the abi4 mutant, results in reduced seed longevity and decreased accumulation of seed-specific transcripts required for production of nutrient reserves and presumed desiccation protectants. Increased ABI4 expression can produce the opposite effect, thereby improving both the nutritional quality and the shelf-life of seeds.

Obtained evidence indicates that ABX4 function is required for vegetative effects of ectopically-expressed ABI3. If these two transcription factors must interact to promote expression of specific target genes, e.g. those involved in production of storage protein and lipid bodies, the ratio of these two regulatory factors could be critical. By modifying expression of ABI4 in concert with ABI3, the effectiveness of the combination can be enhanced, thereby promoting vegetative production of storage proteins and lipids.

Although neither abi3 nor abi4 mutations disrupt stomatal regulation, vegetative expression of ABI3 alone has been shown to enhance stomatal closure in response to drought stress. Vegetative expression of ABI4 can have a comparable effect, resulting in enhanced resistance to drought stress. In addition, many of the seed transcripts whose accumulation is regulated by ABI4 encode proteins thought to play a role in desiccation protection. Increased vegetative production of these gene products can also result in enhanced stress tolerance.

Finally, most promoters commonly used for transgenic expression drive very high levels of expression. While high level expression often produces dramatic results, it may be deleterious to the overall health of the plants. In contrast, the promoter from a regulatory gene, such as ABI4, could facilitate relatively subtle changes in expression of other regulatory genes, especially those not normally expressed during seed development, if it were desirable to extend their effects into seed development.

EXAMPLE 1

Plant Material

This example describes the sources of material used to obtain the abi4 mutant from Arabidopsis thaliana and the procedures used to characterize it genetically and physiologically.

The abscisic acid-insensitive abi4 mutant was isolated from gamma-irradiated Arabidopsis thaliana ecotype Columbia (Col) as described in *Plant Journal*, 5: 765–771, (1994).

Marker lines used for mapping were obtained from the Arabidopsis Biological Resources Center (ABRC) at Ohio State University, Columbus, Ohio.

To determine the genotype at the ABI4 locus or assay the effectiveness of transgenes in complementing the abi4 mutation, ABA sensitivity was scored by germination assays. Seeds (20–100 per treatment) were surface sterilized in 5% hypochlorite, 0.02% Triton X-100, then rinsed 3–4 times with sterile water before plating on minimal medium according to *Mol. Gen. Genet*, 204: 430–434 (1986) (mixed isomers, Sigma) at 3 or 5 $\mu$M in 15×100 mm Petri dishes.

To determine the genotype of any transgene, seedling kanamycin resistance was scored by plating seeds on medium containing 0.5× Murashige-Skoog salts, 1% sucrose, 0.05% MES and 50 $\mu$g/ml kanamycin. The dishes were incubated 1–3 days at 4° C. to break any residual dormancy, then transferred to 22° C. in continuous light or 16 hours light/8 hours dark cycles.

For DNA isolation, plants were grown in pots of soil, composed of a 1:1:1 mix of vermiculite, perlite, and peat moss, supplemented with nutrient salts at 22° C. in continuous light or 16 hours light/8 hours dark cycles. Shoots and rosette leaves were harvested when the shoots started bolting.

For RNA isolation from shoots, flowers, or siliques, plants were grown as described above for DNA isolation. Siliques were harvested as a pooled mixture of developmental stages spanning the full period of embryogeny.

For RNA isolation from roots, plants were grown hydroponically with 3–5 surface sterilized seeds in 25–50 ml Gamborgs B5 medium, shaking at 70–80 rpm. All tissues harvested for nucleic acid extraction were weighed, frozen in liquid nitrogen, and stored at −70° C. until extracted.

To determine the genotype at the ABI4 locus or assay the effectiveness of transgenes in complementing the abi4 mutation, ABA sensitivity was scored by germination assays. Seeds (20–100 per treatment) were surface sterilized in 5% hypochlorite, 0.02% Triton X-100, then rinsed 3–4 times with sterile water before plating on minimal medium according to *Mol. Gen. Genet.*, 204: 430–434 (1986), supplemented with ABA (mixed isomers, Sigma) at 3 or 5 $\mu$M in 15×100 mm Petri dishes.

To determine the genotype of any transgene, seedling kanamycin resistance was scored by plating seeds on medium containing 0.5× Murashige-Skoog salts, 1% sucrose, 0.05% MES and 50 $\mu$g/ml kanamycin. The dishes were incubated 1–3 days at 4∞C to break any residual dormancy, then transferred to 22∞C in continuous light or 16 hours light/8 hours dark cycles.

EXAMPLE 2

Isolation of Recombinant Plants

This example describes a method used for isolation of recombinant plants.

The abi4 mutant was outcrossed to marker lines CS128, CS1, and CS139 carrying the asymmetric leaves (as), *pyrimidine requiring* (py), and eceriferum8 (cer 8) mutations, respectively. The $F_1$ progeny of the crosses were allowed to self-pollinate, producing $F_2$ seed that could be screened for recombinants.

Mapping populations were produced by selecting ABA-insensitive $F_2$ individuals, allowing them to self-pollinate, then screening the resulting $F_3$ families for recombinations with the phenotypically scorable markers py, as, and cer8. To allow direct selection of recombinants between the ABI4 and PY loci, an abi4 py recombinant was backcrossed to wild-type Landsberg erecta (Ler); ABA insensitive $F_2$ progeny that were viable without a thiamine supplement were abi4 PY recombinants.

EXAMPLE 3

Restriction Fragment Length Polymorphism Mapping

This example describes a method used for restriction fragment length polymorphism (RFLP) analysis.

Restriction fragment length polymorphism mapping was performed with $F_3$ and $F_4$ recombinant families. Plant DNA was extracted according to *Methods in Molecular and Cellular Biology*, 3:15–22, (1992).

Approximately 2 $\mu$g of DNA was digested with an appropriate enzyme to distinguish between the parental DNAs. The digested DNA was size-fractioned on a 0.8% agarose gel, denatured and transferred to Zeta-Probe membranes as described in *Mol. Gen. Genet*, 238: 401–408, (1993).

Cosmid, plasmid and phage DNA were isolated as described in *Molecular Cloning: A Laboratory Manual*, 2nd Ed., Cold Spring Harbor, N.Y.: Cold Spring Harbor Laboratory, 1989.

DNA templates were labeled by random priming and filters were hybridized in 5×SSPE, 5×Denhardt's, 0.5% SDS, and 200 $\mu$g/ml herring testes DNA with 1–4×10$^6$ cpm/ml probe added. Enzymes used for scoring Col/Ler RFLPs with the following markers are given in brackets: AtEm6 [SspI], g4514 [HindIII], g5054 [ClaI], m551 [ClaI], g14382 [XhoI], m336 [ClaI].

EXAMPLE 4

Cleaved Amplified Polymorphic Sequence Analysis

This example describes markers used for cleaved amplified polymorphic sequence (CAPS) analysis.

Two CAPS markers, C83 and C14K, were used to fine-map ABI4. Both sequences are located within the region encompassed by CIC10A6. The C83 primers were 5'-GACTGTAAGCTATACTCAC-3' (SEQ ID NO: 13) AND 5'-CGCTCTTCTTCAGACAAGCT-3' (SEQ ID NO: 14) and a polymorphism between Col and Ler DNA was detected with AccI. The C14k primers were 5'-GCGTAAAACGGTTAAACAG-3' (SEQ ID NO: 15) and 5'-GAGAAAGAGGGAAAGTGAG-3' (SEQ ID NO: 16) and a polymorphism between Col and Ler DNA was detected with AflIII digestion. Reaction and cycling conditions were as described in *Plant Journal*, 4:403–410(1993).

EXAMPLE 5

Simple Sequence Length Polymorhpism Analysis

This example describes the procedure used for simple sequence length Polymorhpism (SSLP) analysis.

The microsatellite sequence nga168 (*Genomics*, 19:137–144, (1994)) is polymorphic between the Columbia and Landsberg ecotypes, which are the genetic backgrounds for the abi4 mutant and the marker lines, respectively.

DNA from $F_2$ individuals (10–50 mg leaf tissue per plant), $F_3$ or $F_4$ families was used as a template in PCR amplification of the satellite sequences. PCR mixtures contained approximately 10 ng DNA, 2.5 pmol each primer (MapPairs from Research Genetics, Inc.), 10 mM Tris pH9, 50 mM KCl, 2 mM $MgCl_2$, 0.01% gelatin, 0.1% Triton X-100, 200 $\mu$M dNTPs, and 0.25 units Taq polymerase in a 10 $\mu$l reaction. Reaction products were size-fractionated by electrophoresis through a 6% polyacrylamide, Tris-Borate-EDTA gel according to *Molecular Cloning*, supra.

EXAMPLE 6

Construction of Clones for Complementation Studies

This example describes the procedure used for construction of clones for complementation studies.

The bacterial artificial chromosome (BAC)TAMU7M7 was used as a hybridization probe against the Arabidopsis genomic library constructed in the binary vector pOCA18hyg (*Plant Molecular Biology Manual*, Vol.K3, Gelvin et al., Eds., Kluwer Acad. Publishers, Dordrecht, The Netherlands (1994)), available through the ABRC. Three clones corresponding to the relevant portion of TAMU7M7 were obtained. However, because the predicted genes 4–10 were not fully represented in these clones, a mini-library of TAMU7M7 DNA in the binary cosmid vector pLCD04541 was also constructed.

High molecular weight TAMU7M07 DNA (around 2 $\mu$g) was partially digested with a mixture of Taqα1 and Taq1 methylase, 2 units each (New England Biolabs, Inc., Beverly, Mass.) at 65° C. for 30 minutes to generate DNA fragments ranging from 6–25 kb. 10–20 kb DNA fragments were collected from a 0.5% low melting point (LMP) agarose gel. The pLCD04541 binary cosmid vector (provided by Drs. Clare Lister and Ian Bancroft, John Innes Center, UK) DNA (~2 $\mu$g) was digested with ClaI and dephosphorylated. The 10–20 kb partially digested BAC DNA (100 ng) was ligated to the dephosphorylated vector DNA (100 ng) and transformed into *E. coli* DH5α cells. Transformants were selected on tetracycline LB agar plates containing tetracycline, then screened by colony and Southern hybridizations (*Molecular Cloning*, supra) to identify clones comprising the region of interest. Several of the mini-library clones had internal deletions. Therefore, specific fragments of TAMU7M7 were subcloned into pBIN19 (*Nucleic Acid Res.*, 12: 8711–8721 (1984))to cover individual tightly linked genes.

EXAMPLE 7

Method For Growing Transgenic Plants

This example describes methods used for growing transgenic plants.

Abi4 plants were grown at a density of 3–7 plants per 5 inch pot under 14 hours light L/10 hours dark photoperiods to produce large leafy plants.

Plants were vacuum-infiltrated with an Agrobacterium culture carrying an appropriate plasmid essentially as described in *Science*, 265:1856–1860 (1994).

Seeds were harvested from individual pots and plated on selection medium (0.5×MS salts, 1% sucrose, 50 $\mu$g/ml kanamycin or 40 $\mu$g/ml hygromycin) to identify transgenic progeny. ABA sensitivity and antibiotic resistance were scored in the following generation.

EXAMPLE 8

RNA Isolation and Gel Blot Analysis

This example describes methods used for RNA isolation and gel blotting.

RNA was isolated from seedlings by hot phenol extraction as described previously in *Plant Physiology*, 78: 630–636 (1985). Flower and root RNA was isolated using the Plant RNeasy kit (Qiagen, Chatsworth, Calif.). Silique RNA was isolated by grinding to a fine powder in liquid nitrogen, followed by extraction for 1 hour at 37° C. in 3–5 ml/g of 0.2M Tris, pH 9, 0.4 M NaCl, 25 mM EDTA, 1% SDS, 5 mg/ml polyvinylpolypyrolidone and 5 mg/ml proteinase K per gram of tissue. Proteins and polysaccharides were precipitated by incubation on ice with 18.3 mg/ml $BaCl_2$ and 150 mM Kcl.

After clearing the mixture by 10 minutes centrifugation at 9000 g, RNA was isolated from the supernatant by LiCl precipitation. The pellets were washed in 2M LiCl, then resuspended and reprecipitated with EtOH and NaOAc before a final resuspension in Tris-EDTA. RNA concentration was estimated based on absorbance at 260 and 280 nm.

Total RNA (25 $\mu$g per lane) was size fractionated on 1% agarose Mops-formaldehyde gels, (*Molecular Cloning*, supra) then transferred to Nytran (Schleicher and Schuell) or Hybond N (Amersham) membranes using 20×SSPE as blotting buffer. RNA was bound to the filters by UV-crosslinking (120 mJ/$cm^2$ at 254 nm).

Uniformity of loading and transfer was assayed qualitatively by methylene blue staining of the filters according to *BioTechniques*, 6: 196–200 (1988). The ABI4 RNA was detected by hybridization to clones corresponding to approximately 5' and 3' halves of the coding sequence, labeled by random-priming to a specific activity of $10^8$ cpm/$\mu$g as described in *Nucleic Acid Res.*, 14: 6295 (1987). Hybridization was performed in 7% SDS, 0.5M sodium phosphate, pH 7.2, 1 mM EDTA and 1% BSA at 65° C. 16–24 hours (*PNAS* (USA) 81: 1991–1995 (1984)) in a Hyb-Aid rotisserie oven, with probe added to 2–4×$10^6$ cpm/ml. Filters were washed first in 40 mM sodium phosphate, pH 7.2, 5% SDS, 1 mM EDTA, then in 40 mM sodium phosphate pH 7.2, 1% SDS, 1 mM EDTA with a final wash in 0.2×SSC and 0.1% SDS for 15–60 min each at 65° C. Exposure times were 1–2 weeks.

EXAMPLE 9

DNA Sequence Analysis

This example describes methods used for DNA sequence analysis.

High molecular weight BAC DNA was isolated by a modified alkaline lysis method and was fragmented by nebulization. BAC DNA (4–6 µg) was resuspended in 2 ml of 50 mM Tris, pH 8.0, 15 mM $MgCl_2$, 25% glycerol and transferred into a prepared nebulizer (Inhalation Plastics, Inc., medical product #4207).

DNA was nebulized for 150 secs at 30 psi at the tank outlet. Fragmented DNA sample was concentrated 4.5 fold by 5–6 butanol extractions, then ethanol precipitated. The DNA pellet was washed with 70% cold ethanol, dried and then dissolved in 1×Tris-EDTA at a final concentration of 50 µg/ml. The bulk of the DNA was fragmented into 400 bp to 3-kb pieces, as determined by gel electrophoresis. Ends of the fragmented DNA (~1.5 µg) were filled by Pfu DNA polymerase (Stratagene, La Jolla, Calif., product #200409). The reaction solution was loaded on a 1% low melting point (LMP) agarose (Kodak, #IB70050) gel in 1×TBE and DNA was separated on the gel.

Gel slices containing DNA fragments ranging from 500 bp to 3.0 kb were excised on a long UV light (366 nm) box, then recast in another 1% LMP agarose gel and run in the opposite direction to concentrate the DNA into a very thin band. The DNA band was excised and melted at 65° C. for 10 minutes. The agarose in the solution was digested with Agarase I (New England Biolabs, product #392S) at 40° C. for 15 minutes to pellet the undigested agarose. The digested agarose solution was chilled on ice for 15 minutes and microcentrifuged at 4° C. for 15 minutes to pellet the undigested agarose. The supernatant was transferred into another eppendorf tube and extracted with an equal volume of phenol/chloroform, then chloroform.

The extracted supernatant was mixed with 2 volumes of isopropanol, chilled on ice for 30 minutes and pelletted by microcentrifugation at 48° C. for 15 minutes. The pellet was washed with 70% cold ethanol, dried at RT for 15 minutes, dissolved in 20 1 of 1×Tris-EDTA and stored at 48° C. for later ligation.

pBluescript II KS+vector (Stratagene, #212207) DNA was digested with EcoRV at 37° C. for 3 hours, and dephosphorylated with calf intestinal alkaline phosphatase, (New England Biolabs, product #290S). The dephosphorylated vector DNA (~100 ng) was mixed with the size-selected BAC DNA (~100 ng) and ligated with T4 DNA ligase at 16° C. overnight. After ligation, the ligase was heat inhibited at 65° C. for 10 minutes. DNA in the ligation solution was electrotransformed into *E. coli* DH5 competent cells by using a BIO-RAD gene pulser. Transformants were recovered in 1 ml of SOC at 37° C. with shaking at 300 rpm for 1 hour. Transformants in the recovery solution were mixed with an equal volume of 30% glycerol, divided into aliquots (100 ml) and stored at –80° C. for later use. The frozen transformant stock was thawed briefly and diluted 50 times with LB liquid medium and then plated onto selective LB agar plated containing 50 µg/ml ampicillin.

Recombinants were identified using a blue-white screening system. White colonies were inoculated into 96-well titer plates (each well containing 1.3 ml of liquid LB medium ) and cultured at 37° C. with shaking at 300 rpm for 22 hours.

Plasmid DNA was isolated by using rapid extraction alkaline plasmid kits (QIAGEN, product #26173), dissolved in 50 µl of double distilled water to be used as DNA templates for sequencing. DNA was sequenced on a 377 DNA sequencer (ABI prism™).

The Phred, Phrap and Consed sequence assembly and viewing programs (Phil Green unpublished, HTTP://www.genome.washington.edu/) were used to remove BAC vector sequences and to assemble contigs. After large sequence contigs assembled and only a few gaps remained, the gaps were closed by amplifying the intervening DNA by PCR from the original BAC DNA, using primers based on adjacent sequences. The PCR products were sequenced on a long-range sequencer ABI 377 using dye terminator chemistry as described by the manufacturer Perkin Elmer.

EXAMPLE 10

3'Rapid Amplification of cDNA Ends (RACE) Methods

This example describes methods used for 3'RACE cDNA amplification.

Total RNA (5 µg) was used as template for reverse transcription using a 3'RACE kit (Gibco-BRL). Following first strand synthesis and RNase H treatment, cDNAs were amplified using the universal adapter primer (UAP) and a gene specific primer annealing 53 nt 5' to the start of the ABI4 ORF. Amplified products were size fractionated on a 1% agarose gel, blotted and hybridized to an internal fragment of the ABI4 gene.

A nested primer, annealing 30 nt 5' to the presumed initiating codon, was used to amplify cDNAs from a plug of sized DNA corresponding to the region of hybridization.

The amplification reactions contained 20 mM Tris-HCl, pH 8.4, 50 mM KCl, 1.5 mM MgCl2, 200 nM each primer, 200 M each deoxynucleotide triphosphate, and 0.05 U/mL Taq polymerase. The polymerase was added after a 3 minutes incubation at 94° C. for "hot start" amplification. Cycling conditions were 30 cycles of (45 sec at 94° C., 1 minute at 57.5° C., 2 min. at 72° C.)

The cDNAs were gel-purified with Gene-Clean (Bio 101, La Jolla, Calif.) according to the manufacturers instructions.

The ends were blunted by fill-in reactions with the Klenow fragment of DNA polymerase I, followed by treatment with T4 polynucleotide kinase as described in (*Molecular Cloning*, supra). cDNAs were ligated into pBS kt (Stratagene) following digestion with EcoRV and dephosphorylation, then transformed into *E. coli* strain DH5α.

Transformants were selected on ampicillin X-gal LB agar plates. White colonies were screened for the presence of appropriate inserts by restriction mapping of plasmid DNA.

EXAMPLE 11

Construction of 2×35S::ABI3, abi4 Lines

This example describes construction of genetic lines used to test for interactions between ectopic expression of ABI3 and the abi4 mutation.

To obtain lines with a 2×35S::ABI3 transgene in the abi4 mutant background, recombinant abi4 lines carrying the closely linked py mutation were crossed to the transgenic lines C7AX6 and C7A19 described as C7AX6 and C7A19 in *Plant Cell*, 6:1567–1582 (1994). Kanamycin resistant $F_2$ individuals were selected and screened for thiamine auxotrophy resulting from the py mutation. Families homozygous for the transgene were identified as 100% kanamycin resistant in the $F_3$ generation.

EXAMPLE 12

Root Growth Sensitivity to ABA

This example describes the effects of ectopic expression of ABI3 or ABI4 on sensitivity to ABA for inhibition of root growth. Construction of the ABI4 ectopic expression lines is described in Example 14.

After 2 days growth on hormone-free medium, abi4, 2×35S::ABI3, 35S::ABI4 or control genotype seedlings were transferred to fresh media containing ABA at the indicated concentrations. Plates were incubated vertically, 180∞ relative to the original orientation of the roots, and new growth was measured after 4 days. Growth on ABA is expressed as a % of growth on the control medium, while growth on control medium is expressed in mm. Results are shown in FIGS. 9 and 11.

EXAMPLE 13

ABA-Induced, ABI3- and ABI4-Dependent Vegetative Expression of Embryonic Transcripts This example describes the effects of the abi4 mutation on ABA-induced, ABI3-dependent vegetative expression of embryonic transcripts. In addition, it describes the effects of ABI4 ectopic expression on ABA-inducibility of vegetative expression of embryonic transcripts.

After 11 d growth on hormone-free medium, abi4,2× 35S::ABI3, 35S::ABI4, or control genotype plants were incubated for 2 days on plates with or without 50 uM ABA prior to harvest.

RNA was extracted and analyzed by Northern blots as described in Example 8, except that filters were hybridized to cDNA clones for AtEml, At2S, CRC, RAB18 and ABI3. Six genotypes were compared: Col and abi4, each with no transgene, weakly expressed, and strongly expressed 2×35S::ABI3 transgenes. Results are shown in FIG. 10. In addition, several independent lines carrying the 35S::ABI4 transgene, described in Example 14, were compared with a nontransgenic control. In this experiment, the clones used for hybridization correspond to the AtEml, AtEm6, and CRC genes. Results are shown in FIG. 12.

EXAMPLE 14

Construction of 35S::ABI4 Ectopic Expression Lines

This example describes construction of 35S::ABI4 fusion genes and production of plants carrying these transgenes.

Two genomic fragments containing the entire ABI4 coding sequence and some flanking DNA were cloned into the BglII site of pGA643 (Plant Molecular Biology Manual, S. B. Gelvin, R. A. Schilperoort, Eds., Dordrecht: Kluwer Academic Publishers, A3:1–19 (1988)) following treatment with the Klenow fragment of DNA polymerase to create blunt-ended DNA fragments for ligation.

One of the fragments used was a 1.9 kb SspI fragment that includes 0.5 kb 5' to the initiating codon and 0.4 kb downstream of the stop codon, including all polyadenylation sites observed in the cDNAs produced by RACE, as described in Example 10.

The other fragment was produced by PCR amplification of a subregion of the SspI fragment and has the same 3' end, but contains only 53 bp 5' to the initiating codon. The accuracy of the amplification was confirmed by sequencing the subcloned product. Plasmid DNA was isolated by alkaline lysis extraction, then purified on QIAGEN columns, and eluted in nanopure-filtered water to be used as DNA templates for sequencing. The DNA was sequenced at the Iowa State University DNA sequencing facility for automated sequencing using dye terminator chemistry as described by the manufacturer Perkin Elmer.

The 35S::ABI4 fusions in the pGA643 vector were transferred into competent Agrobacterium tumefaciens GV3101 by direct transformation as described in *Plant Molecular Biology Manual*, supra. Wild-type plants were vacuum-infiltrated with an Agrobacterium culture carrying an appropriate plasmid essentially as described in Example 7. Transgenic progeny were selected by growth on kanamycin, also as described in Example 7.

---

What is claimed is:

1. An isolated DNA sequence comprising a nucleotide sequence identified as SEQ ID NO: 1 or a mutant thereof comprising a nucleotide sequence identified as SEQ ID NO: 3.

2. The sequence of claim 1 identified as SEQ ID NO: 2 and deposited at GenBank under Accession Number AF040959 and encoding a predicted amino acid sequence identified as SEQ ID NO: 2.

3. A recombinant nucleotide sequence comprising a nucleotide sequence depicting a mutant ABI4 gene set forth in SEQ ID NO: 3.

4. A method for increasing storage reserves in seeds and dessication protectants in vegetative tissue in a recipient seed or vegetative tissue by altering expression of the ABI4 gene, said method comprising steps:

(a) constructing the ABI4 transgene by fusing ABI4 coding sequence comprising SEQ ID NO: 1 to a regulatory sequence for overexpression of said coding sequence in embryos or shoots derived from said recipient seed or vegetative tissue;

(b) transferring the transgene constructed in step (a) into the recipient seed by Agrobacterium-mediated transformation, by biolistic transformation, or by electroporation; and (c) selecting a transgenic individual overexpressing said coding sequence from primary transformant lines by scoring for resistance to antibiotics and herbicides.

5. The method of claim 4 wherein the seed or vegetative tissue is soybean, cotton, barley or wheat.

6. The method of claim 5 wherein said regulatory sequence is a promoter or a transcriptional enhancer and wherein said promoter is a late embryogenesis abundant gene or a highly expressed light regulated gene, and wherein said transcriptional enhancer is a cis-acting sequence required for embryonic, ABA-regulated or light-regulated expression.

7. The method of claim 6 wherein the highly expressed gene is the Em gene, wherein the highly expressed light regulated gene is the rbcS or cab gene, and wherein the transcriptional enhancer an ACGT or RY repeat.

8. The method of claim 7 wherein the transgene is transferred into recipient plant by Agrobacterium-mediated transformation.

9. The method of claim 8 wherein the selected transgenic individual is homozygous for the ABI4 transgene.

10. The method of claim 9 wherein the primary transformant lines are identified by scoring the resistance to antibiotics.

11. The method of claim 10 wherein the antibiotic resistance of the transgenic individual is tested against kanamycin, neomycin, hygromycin or streptomycin.

12. The method of claim 4 wherein the transgenic seed or vegetative tissue is a dicot or monocot.

13. A method for production of a recombinant transgenic seed or vegetative tissue having increased storage reserves and dessication protectants, said method comprising a step of overexpressing a protein comprising an amino acid sequence identified as SEQ ID NO: 2 in a seed or vegetative tissue infiltrated with a culture of Agrobacterium tumefaciens transformed with a plasmid comprising a nucleotide sequence encoding SEQ ID NO: 1.

* * * * *

SEQUENCE LISTING

<160> NUMBER OF SEQ ID NOS: 16

<210> SEQ ID NO 1
<211> LENGTH: 1500
<212> TYPE: DNA
<213> ORGANISM: Arabidopsis
<220> FEATURE:
<221> NAME/KEY: CDS
<222> LOCATION: (151)..(1134)

<400> SEQUENCE: 1

```
aatcgaccat tcacaacgat gacattcaaa cactcttcag tttcccttcc ttcttgattc      60
gtcctctcca ctattttct caatttcttt aatctctctc tttctctctc tacttcctct     120
tcctcttctt cttcttcttc ttcttcatct atg gac cct tta gct tcc caa cat     174
                                    Met Asp Pro Leu Ala Ser Gln His
                                    1               5 caa cac aac cat ctg gaa gat aat aac caa acc cta acc cat aat aat      222
Gln His Asn His Leu Glu Asp Asn Asn Gln Thr Leu Thr His Asn Asn
    10              15                  20
```

-continued

| | | |
|---|---|---|
| cct caa tcc gat tcc acc acc gac tca tca act tcc tcc gct caa cgc<br>Pro Gln Ser Asp Ser Thr Thr Asp Ser Ser Thr Ser Ser Ala Gln Arg<br>25                            30                      35                      40 | 270 |
| aaa cgc aaa ggc aaa ggt ggt ccg gac aac tcc aag ttc cgt tac cgt<br>Lys Arg Lys Gly Lys Gly Gly Pro Asp Asn Ser Lys Phe Arg Tyr Arg<br>                    45                      50                      55 | 318 |
| ggc gtt cga caa aga agc tgg ggc aaa tgg gtc gcc gag atc cga gag<br>Gly Val Arg Gln Arg Ser Trp Gly Lys Trp Val Ala Glu Ile Arg Glu<br>            60                      65                      70 | 366 |
| cca cgt aag cgc act cgc aag tgg ctt ggt act ttc gca acc gcc gaa<br>Pro Arg Lys Arg Thr Arg Lys Trp Leu Gly Thr Phe Ala Thr Ala Glu<br>              75                      80                      85 | 414 |
| gac gcc gca cgt gcc tac gac cgg gct gcc gtt tac cta tac ggg tca<br>Asp Ala Ala Arg Ala Tyr Asp Arg Ala Ala Val Tyr Leu Tyr Gly Ser<br>    90                      95                      100 | 462 |
| cgt gct cag ctc aac tta acc cct tcg tct cct tcc tcc gtc tct tcc<br>Arg Ala Gln Leu Asn Leu Thr Pro Ser Ser Pro Ser Ser Val Ser Ser<br>105                      110                      115                      120 | 510 |
| tct tcc tcc tcc gtc tcc gcc gct tct tct cct tcc acc tcc tct tcc<br>Ser Ser Ser Ser Val Ser Ala Ala Ser Ser Pro Ser Thr Ser Ser Ser<br>                      125                      130                      135 | 558 |
| tcc act caa acc cta aga cct ctc ctc cct cgc ccc gcc gcc gcc acc<br>Ser Thr Gln Thr Leu Arg Pro Leu Leu Pro Arg Pro Ala Ala Ala Thr<br>            140                      145                      150 | 606 |
| gta gga gga gga gcc aac ttt ggt ccg tac ggt atc cct ttt aac aac<br>Val Gly Gly Gly Ala Asn Phe Gly Pro Tyr Gly Ile Pro Phe Asn Asn<br>              155                      160                      165 | 654 |
| aac atc ttc ctt aat ggt ggg acc tct atg tta tgc cct agt tat ggt<br>Asn Ile Phe Leu Asn Gly Gly Thr Ser Met Leu Cys Pro Ser Tyr Gly<br>     170                      175                      180 | 702 |
| ttt ttc cct caa caa caa caa caa caa aat cag atg gtc cag atg gga<br>Phe Phe Pro Gln Gln Gln Gln Gln Gln Asn Gln Met Val Gln Met Gly<br>185                      190                      195                      200 | 750 |
| caa ttc caa cac caa cag tat cag aat ctt cat tct aat act aac aat<br>Gln Phe Gln His Gln Gln Tyr Gln Asn Leu His Ser Asn Thr Asn Asn<br>                205                      210                      215 | 798 |
| aac aag att tct gac atc gag ctc act gat gtt ccg gta act aat tcg<br>Asn Lys Ile Ser Asp Ile Glu Leu Thr Asp Val Pro Val Thr Asn Ser<br>                      220                      225                      230 | 846 |
| act tcg ttt cat cat gag gtg gcg tta ggg cag gaa caa gga gga agt<br>Thr Ser Phe His His Glu Val Ala Leu Gly Gln Glu Gln Gly Gly Ser<br>                235                      240                      245 | 894 |
| ggg tgt aat aat aat agt tcg atg gag gat ttg aac tct cta gct ggt<br>Gly Cys Asn Asn Asn Ser Ser Met Glu Asp Leu Asn Ser Leu Ala Gly<br>250                      255                      260 | 942 |
| tcg gtg ggt tcg agt cta tca ata act cat cca ccg ccg ttg gtt gat<br>Ser Val Gly Ser Ser Leu Ser Ile Thr His Pro Pro Pro Leu Val Asp<br>265                      270                      275                      280 | 990 |
| ccg gta tgt tct atg ggt ctg gat ccg ggt tat atg gtt gga gat gga<br>Pro Val Cys Ser Met Gly Leu Asp Pro Gly Tyr Met Val Gly Asp Gly<br>                      285                      290                      295 | 1038 |
| tct tcg acc att tgg cct ttt gga gga gaa gaa gaa tat agt cat aat<br>Ser Ser Thr Ile Trp Pro Phe Gly Gly Glu Glu Glu Tyr Ser His Asn<br>            300                      305                      310 | 1086 |
| tgg ggg agt att tgg gat ttt att gat ccc atc ttg ggg gaa ttc tat<br>Trp Gly Ser Ile Trp Asp Phe Ile Asp Pro Ile Leu Gly Glu Phe Tyr<br>              315                      320                      325 | 1134 |
| taatttgttt ttgtggaaga tcatattata tacgatgagc atccctaagg tcggtcaaga | 1194 |
| gcattggaga ttcattgttg agaggaatca aagagattgc attctatgag gagctctgca | 1254 |

```
tgcaaaattt tggaggattt ttttactacc tatagagata aataagaggg tattttatt    1314 attttttga agattttat tttcaaggaa ttcgtaaaag agattacggt tccaataaag     1374
tatgtatatg tggaagagaa tcggaggaga tggtggaaaa ttgtatggga atttattgg    1434 ttcaacactt ccttcacagt gtgcctacct taatatataa ttattgatag gatatgataa   1494
tttctg                                                              1500
```

<210> SEQ ID NO 2
<211> LENGTH: 328
<212> TYPE: PRT
<213> ORGANISM: Arabidopsis

<400> SEQUENCE: 2

```
Met Asp Pro Leu Ala Ser Gln His Gln His Asn His Leu Glu Asp Asn
  1               5                  10                  15

Asn Gln Thr Leu Thr His Asn Asn Pro Gln Ser Asp Ser Thr Thr Asp
             20                  25                  30

Ser Ser Thr Ser Ser Ala Gln Arg Lys Arg Lys Gly Lys Gly Gly Pro
         35                  40                  45

Asp Asn Ser Lys Phe Arg Tyr Arg Gly Val Arg Gln Arg Ser Trp Gly
     50                  55                  60

Lys Trp Val Ala Glu Ile Arg Glu Pro Arg Lys Arg Thr Arg Lys Trp
 65                  70                  75                  80

Leu Gly Thr Phe Ala Thr Ala Glu Asp Ala Ala Arg Ala Tyr Asp Arg
                 85                  90                  95

Ala Ala Val Tyr Leu Tyr Gly Ser Arg Ala Gln Leu Asn Leu Thr Pro
            100                 105                 110

Ser Ser Pro Ser Ser Val Ser Ser Ser Ser Val Ser Ala Ala
            115                 120                 125

Ser Ser Pro Ser Thr Ser Ser Ser Thr Gln Thr Leu Arg Pro Leu
            130                 135                 140

Leu Pro Arg Pro Ala Ala Ala Thr Val Gly Gly Gly Ala Asn Phe Gly
145                 150                 155                 160

Pro Tyr Gly Ile Pro Phe Asn Asn Ile Phe Leu Asn Gly Gly Thr
                165                 170                 175

Ser Met Leu Cys Pro Ser Tyr Gly Phe Phe Pro Gln Gln Gln Gln
            180                 185                 190

Gln Asn Gln Met Val Gln Met Gly Gln Phe Gln His Gln Gln Tyr Gln
            195                 200                 205

Asn Leu His Ser Asn Thr Asn Asn Lys Ile Ser Asp Ile Glu Leu
            210                 215                 220

Thr Asp Val Pro Val Thr Asn Ser Thr Ser Phe His His Glu Val Ala
225                 230                 235                 240

Leu Gly Gln Glu Gln Gly Gly Ser Gly Cys Asn Asn Ser Ser Met
                245                 250                 255

Glu Asp Leu Asn Ser Leu Ala Gly Ser Val Gly Ser Ser Leu Ser Ile
            260                 265                 270

Thr His Pro Pro Leu Val Asp Pro Val Cys Ser Met Gly Leu Asp
            275                 280                 285

Pro Gly Tyr Met Val Gly Asp Gly Ser Ser Thr Ile Trp Pro Phe Gly
            290                 295                 300

Gly Glu Glu Glu Tyr Ser His Asn Trp Gly Ser Ile Trp Asp Phe Ile
305                 310                 315                 320
```

Asp Pro Ile Leu Gly Glu Phe Tyr
            325

<210> SEQ ID NO 3
<211> LENGTH: 1499
<212> TYPE: DNA
<213> ORGANISM: Arabidopsis

<400> SEQUENCE: 3

```
aatcgaccat tcacaacgat gacattcaaa cactcttcag tttcccttcc ttcttgattc      60
gtcctctcca ctattttct caatttcttt aatctctctc tttctctctc tacttcctct     120
tcctcttctt cttcttcttc ttcttcatct atggacccctt tagcttccca acatcaacac    180
aaccatctgg aagataataa ccaaacccta acccataata atcctcaatc cgattccacc     240
accgactcat caacttcctc cgctcaacgc aaacgcaaag gcaaaggtgg tccggacaac     300
tccaagttcc gttaccgtgg cgttcgacaa agaagctggg gcaaatgggt cgccgagatc     360
cgagagccac gtaagcgcac tcgcaagtgg cttggtactt tcgcaaccgc cgaagacgcc     420
gcacgtgcct acgaccgggc tgccgtttac ctatacgggt cacgtgctca gctcaactta     480
accccttcgt ctccttcctc cgtctcttcc tcttcctcct ccgtctccgc cgcttcttct     540
ccttccacct cctcttcccc actcaaaccc taagacctct cctccctcgc cccgccgccg     600
ccaccgtagg aggaggagcc aactttggtc cgtacggtat ccctttttaac aacaacatct    660
tccttaatgg tgggacctct atgttatgcc ctagttatgg ttttttccct caacaacaac    720
aacaacaaaa tcagatggtc cagatgggac aattccaaca ccaacagtat cagaatcttc     780
attctaatac taacaataac aagatttctg acatcgagct cactgatgtt ccggtaacta     840
attcgacttc gtttcatcat gaggtggcgt tagggcagga acaaggagga agtgggtgta     900
ataataatag ttcgatggag gatttgaact ctctagctgg ttcggtgggt tcgagtctat     960
caataactca tccaccgccg ttggttgatc cggtatgttc tatgggtctg gatccgggtt    1020
atatggttgg agatggatct tcgaccattt ggccttttgg aggagaagaa gaatatagtc    1080
ataattgggg gagtatttgg gattttattg atcccatctt gggggaattc tattaatttg    1140
tttttgtgga agatcatatt atatacgatg agcatcccta aggtcggtca agagcattgg    1200
agattcattg ttgagaggaa tcaaagagat tgcattctat gaggagctct gcatgcaaaa    1260
ttttggagga ttttttttact acctatagag ataaataaga gggtatttttt attattttt    1320
tgaagattt tattttcaag gaattcgtaa aagagattac ggttccaata aagtatgtat     1380
atgtggaaga gaatcggagg agatggtgga aagttgtatg ggaattttat tggttcaaca    1440
cttccttcac agtgtgccta ccttaatata taattattga taggatatga taatttctg    1499
```

<210> SEQ ID NO 4
<211> LENGTH: 59
<212> TYPE: PRT
<213> ORGANISM: Arabidopsis

<400> SEQUENCE: 4

Tyr Arg Gly Val Arg Gln Arg Ser Trp Gly Lys Trp Val Ala Glu Ile
 1               5                  10                  15

Arg Glu Pro Arg Lys Arg Thr Arg Lys Trp Leu Gly Thr Phe Ala Thr
            20                  25                  30

Ala Glu Asp Ala Ala Arg Ala Tyr Asp Arg Ala Ala Val Tyr Leu Tyr
        35                  40                  45

Gly Ser Arg Ala Gln Leu Asn Leu Thr Pro Ser
    50                  55

-continued

```
                50                  55

<210> SEQ ID NO 5
<211> LENGTH: 59
<212> TYPE: PRT
<213> ORGANISM: AP2 domain protein

<400> SEQUENCE: 5

Tyr Arg Gly Val Arg Gln Arg Asn Ser Gly Lys Trp Val Ser Glu Val
  1               5                  10                  15

Arg Glu Pro Asn Lys Lys Thr Arg Ile Trp Leu Gly Thr Phe Gln Thr
                 20                  25                  30

Ala Glu His Ala Ala Arg Ala His Asp Val Ala Ala Leu Ala Leu Arg
             35                  40                  45

Gly Arg Ser Ala Cys Leu Asn Phe Ala Asp Ser
         50                  55

<210> SEQ ID NO 6
<211> LENGTH: 59
<212> TYPE: PRT
<213> ORGANISM: AP2 domain protein

<400> SEQUENCE: 6

Tyr Arg Gly Val Arg Gln Arg His Trp Gly Ser Trp Val Ser Glu Ile
  1               5                  10                  15

Arg His Ser Ile Leu Lys Thr Arg Ile Trp Gln Gly Thr Phe Glu Ser
                 20                  25                  30

Ala Glu Asp Ala Ala Arg Ala Tyr Asp Glu Ala Ala Arg Leu Met Cys
             35                  40                  45

Gly Thr Arg Ala Arg Thr Asn Phe Pro Tyr Asn
         50                  55

<210> SEQ ID NO 7
<211> LENGTH: 59
<212> TYPE: PRT
<213> ORGANISM: AP2 domain protein

<400> SEQUENCE: 7

Tyr Arg Gly Val Arg Gln Arg Pro Trp Gly Lys Trp Ala Ala Glu Ile
  1               5                  10                  15

Arg Asp Pro Asn Lys Ala Ala Arg Val Trp Leu Gly Thr Phe Asp Thr
                 20                  25                  30

Ala Glu Glu Ala Ala Leu Ala Tyr Asp Lys Ala Ala Phe Glu Phe Arg
             35                  40                  45

Gly His Lys Ala Lys Leu Asn Phe Pro Glu His
         50                  55

<210> SEQ ID NO 8
<211> LENGTH: 59
<212> TYPE: PRT
<213> ORGANISM: AP2 domain protein

<400> SEQUENCE: 8

Tyr Arg Gly Val Arg Lys Arg Asn Trp Gly Lys Trp Val Ser Glu Ile
  1               5                  10                  15

Arg Glu Pro Arg Lys Lys Ser Arg Ile Trp Leu Gly Thr Phe Pro Ser
                 20                  25                  30

Pro Glu Met Ala Ala Arg Ala His Asp Val Ala Ala Leu Ser Ile Lys
             35                  40                  45
```

Gly Ala Ser Ala Ile Leu Asn Phe Pro Asp Leu
        50                  55

<210> SEQ ID NO 9
<211> LENGTH: 60
<212> TYPE: PRT
<213> ORGANISM: AP2 domain protein

<400> SEQUENCE: 9

Tyr Arg Gly Val Arg Arg Pro Trp Gly Lys Phe Ala Ala Glu Ile
 1               5                  10                  15

Arg Asp Pro Ala Lys Asn Gly Ala Arg Val Trp Leu Gly Thr Tyr Glu
                20                  25                  30

Thr Asp Glu Glu Ala Ala Ile Ala Tyr Asp Lys Ala Ala Tyr Arg Met
            35                  40                  45

Arg Gly Ser Lys Ala His Leu Asn Phe Pro His Arg
        50                  55                  60

<210> SEQ ID NO 10
<211> LENGTH: 59
<212> TYPE: PRT
<213> ORGANISM: AP2 domain protein

<400> SEQUENCE: 10

Tyr Arg Gly Ile Arg Lys Arg Pro Trp Gly Lys Trp Ala Ala Glu Ile
 1               5                  10                  15

Arg Asp Pro Arg Lys Gly Val Arg Val Trp Leu Gly Thr Phe Asn Thr
                20                  25                  30

Ala Glu Glu Ala Ala Met Ala Tyr Asp Val Ala Ala Lys Gln Ile Arg
            35                  40                  45

Gly Asp Lys Ala Lys Leu Asn Phe Pro Asp Leu
        50                  55

<210> SEQ ID NO 11
<211> LENGTH: 61
<212> TYPE: PRT
<213> ORGANISM: AP2 domain protein

<400> SEQUENCE: 11

Tyr Arg Gly Val Thr Phe Tyr Arg Arg Thr Gly Arg Trp Glu Ser His
 1               5                  10                  15

Ile Trp Asp Cys Gly Lys Arg Thr Gln Val Tyr Trp Leu Gly Thr Asp
                20                  25                  30

Ala Thr His Ala Asp Ala Ala Arg Ala Tyr Asp Arg Ala Ile Lys Phe
            35                  40                  45

Arg Tyr Val Glu Arg Asp Ile Leu Phe Asn Ile Asp Asp
        50                  55                  60

<210> SEQ ID NO 12
<211> LENGTH: 60
<212> TYPE: PRT
<213> ORGANISM: AP2 domain protein

<400> SEQUENCE: 12

Tyr Arg Gly Val Thr Leu His Lys Cys Trp Arg Lys Glu Val Arg Met
 1               5                  10                  15

Gly Gln Phe Leu Gly Lys Lys Tyr Val Tyr Leu Gly Leu Phe Asp Ala
                20                  25                  30

Glu Val Glu Asp Ala Ala Arg Ala Tyr Lys Arg Ala Ile Lys Cys Asn
            35                  40                  45

```
Tyr Lys Asp Arg Val Thr Leu Phe Asp Pro Ser Ile
    50                  55                  60

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 13
gactgtaagc tatactcac                                              19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 14
cgctcttctt cagacaagct                                             20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 15
gcgtaaaacg gttaaacag                                              19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 16
gagaaagagg gaaagtgag                                              19
```